US012274588B2

(12) United States Patent
Blair et al.

(10) Patent No.: US 12,274,588 B2
(45) Date of Patent: Apr. 15, 2025

(54) MULTI-MODE IMAGING MARKERS

(71) Applicant: View Point Medical, Inc., Carlsbad, CA (US)

(72) Inventors: William Blair, San Diego, CA (US); Mike Jones, San Clemente, CA (US); John Merritt, San Clemente, CA (US)

(73) Assignee: View Point Medical, Inc., Carlsbad, CA (US)

( * ) Notice: Subject to any disclaimer, the term of this patent is extended or adjusted under 35 U.S.C. 154(b) by 0 days.

(21) Appl. No.: 18/646,526

(22) Filed: Apr. 25, 2024

(65) Prior Publication Data

US 2024/0277446 A1 Aug. 22, 2024

Related U.S. Application Data

(63) Continuation of application No. 17/473,820, filed on Sep. 13, 2021, now Pat. No. 11,986,359, which is a continuation of application No. 15/946,479, filed on Apr. 5, 2018, now Pat. No. 11,116,599.

(60) Provisional application No. 62/483,274, filed on Apr. 7, 2017, provisional application No. 62/645,677, filed on Mar. 20, 2018.

(51) Int. Cl.
A61B 6/12 (2006.01)
A61B 6/00 (2006.01)
A61B 90/00 (2016.01)
A61B 6/50 (2024.01)
A61B 17/00 (2006.01)

(52) U.S. Cl.
CPC .............. *A61B 90/39* (2016.02); *A61B 6/12* (2013.01); *A61B 6/487* (2013.01); *A61B 6/502* (2013.01); *A61B 2017/00898* (2013.01); *A61B 2017/00938* (2013.01); *A61B 2090/3908* (2016.02); *A61B 2090/3925* (2016.02); *A61B 2090/3937* (2016.02); *A61B 2090/3954* (2016.02); *A61B 2090/3966* (2016.02); *A61B 2090/3987* (2016.02); *A61B 2090/3995* (2016.02)

(58) Field of Classification Search
CPC ........... A61B 90/39; A61B 6/12; A61B 6/487; A61B 2017/00938; A61B 2090/3937; A61B 2090/3925; A61B 2090/3995
See application file for complete search history.

(56) References Cited

U.S. PATENT DOCUMENTS

| | | | |
|---|---|---|---|
| 4,234,752 A | 11/1980 | Wu et al. | |
| 5,512,094 A | 4/1996 | Linton | |
| 6,161,034 A | 12/2000 | Burbank et al. | |
| 6,174,330 B1 | 1/2001 | Stinson | |
| 6,221,326 B1 | 4/2001 | Amiche | |
| 6,235,801 B1 | 5/2001 | Morales et al. | |
| 6,331,166 B1 | 12/2001 | Burbank et al. | |
| 6,347,241 B2 | 2/2002 | Burbank et al. | |
| 6,427,081 B1 | 7/2002 | Burbank et al. | |
| 6,494,841 B1 | 12/2002 | Thomas et al. | |
| 6,567,689 B2 | 5/2003 | Burbank et al. | |
| 6,699,206 B2 | 3/2004 | Burbank et al. | |
| 6,725,083 B1 | 4/2004 | Burbank et al. | |
| 6,862,470 B2 | 3/2005 | Burbank et al. | |
| 6,996,433 B2 | 2/2006 | Burbank et al. | |
| 7,322,938 B2 | 1/2008 | Burbank et al. | |
| 7,322,939 B2 | 1/2008 | Burbank et al. | |
| 7,322,940 B2 | 1/2008 | Burbank et al. | |
| 7,651,505 B2 | 1/2010 | Lubock et al. | |
| 7,792,569 B2 | 9/2010 | Burbank et al. | |
| 7,871,438 B2 | 1/2011 | Corbitt | |
| 7,970,454 B2 | 6/2011 | Jones et al. | |
| 7,983,734 B2 | 7/2011 | Jones et al. | |
| 8,157,862 B2 | 4/2012 | Corbitt | |
| 8,177,792 B2 | 5/2012 | Lubock et al. | |
| 8,219,182 B2 | 7/2012 | Burbank et al. | |
| 8,224,424 B2 | 7/2012 | Burbank et al. | |
| 8,361,082 B2 | 1/2013 | Jones et al. | |
| 8,440,229 B2 | 5/2013 | Trogler et al. | |
| 8,498,693 B2 | 7/2013 | Jones et al. | |
| 8,626,269 B2 | 1/2014 | Jones et al. | |
| 8,626,270 B2 | 1/2014 | Burbank et al. | |
| 8,668,737 B2 | 3/2014 | Corbitt | |
| 8,680,498 B2 | 3/2014 | Corbitt et al. | |
| 8,718,745 B2 | 5/2014 | Burbank et al. | |
| 8,784,433 B2 | 7/2014 | Lubock et al. | |

(Continued)

FOREIGN PATENT DOCUMENTS

CN 102266592 A 12/2011
CN 102389576 A 3/2012
(Continued)

OTHER PUBLICATIONS

Chih-Chia Huang et al. Shell-by-shell synthesis of multi-shelled mesoporous silica nanospheres for optical imaging and drug delivery, Biomaterials, 32, 556-564. (Year: 2011).*

Chang, Song-Yuan, et al., "Preparation and Properties of Tailored Morphology, Monodisperse Colloidal Silica-Cadmium Sulfide Nanocomposites,", J. Am. Chem. Soc., Jul. 1994, 116 (15), pp. 6739-6744.

Cornelissen, Jeroen J.L.M, et al., "Versatile synthesis of nanometer sized hollow silica spheres," Chem. Commun., 2003,8, 1010-1011.

(Continued)

*Primary Examiner* — Johann R Richter
*Assistant Examiner* — Jagadishwar R Samala
(74) *Attorney, Agent, or Firm* — Cozen O'Connor

(57) ABSTRACT

Imaging marker embodiments that may be used for marking sites within a patient's body are discussed. Some imaging marker embodiments are particularly useful for imaging with ultrasound imaging modalities and some imaging marker embodiments may be suitable for imaging with multiple modes of imaging modalities. Method embodiments for making and using imaging markers are also discussed herein.

19 Claims, 27 Drawing Sheets

(56) References Cited

U.S. PATENT DOCUMENTS

| | | | |
|---|---|---|---|
| 8,880,154 | B2 | 11/2014 | Jones et al. |
| 9,044,162 | B2 | 6/2015 | Jones et al. |
| 9,149,341 | B2 | 10/2015 | Jones et al. |
| 9,220,585 | B2 | 12/2015 | Horton et al. |
| 9,327,061 | B2 | 5/2016 | Govil et al. |
| 9,480,554 | B2 | 11/2016 | Corbitt |
| 9,579,077 | B2 | 2/2017 | Casanova et al. |
| 9,743,909 | B1 | 8/2017 | Sapozhnikov et al. |
| 9,801,688 | B2 | 10/2017 | Jones et al. |
| 9,820,824 | B2 | 11/2017 | Jones et al. |
| 9,861,294 | B2 | 1/2018 | Jones et al. |
| 10,172,674 | B2 | 1/2019 | Jones et al. |
| 2003/0204137 | A1 | 10/2003 | Chesbrough et al. |
| 2004/0116806 | A1 | 6/2004 | Burbank et al. |
| 2004/0187524 | A1 | 9/2004 | Sen et al. |
| 2004/0236213 | A1 | 11/2004 | Jones et al. |
| 2005/0008578 | A1 | 1/2005 | Schmidt |
| 2005/0063908 | A1 | 3/2005 | Burbank et al. |
| 2005/0158390 | A1 | 7/2005 | Rana et al. |
| 2006/0079597 | A1 | 4/2006 | Muratoglu et al. |
| 2006/0293581 | A1 | 12/2006 | Plewes et al. |
| 2007/0276252 | A1 | 11/2007 | Kolasa et al. |
| 2008/0097207 | A1 | 4/2008 | Cai |
| 2008/0102029 | A1 | 5/2008 | Fritz et al. |
| 2011/0196285 | A1 | 8/2011 | Chen et al. |
| 2011/0229576 | A1 | 9/2011 | Trogler et al. |
| 2012/0052012 | A1* | 3/2012 | Chenite .................. A61K 35/14 424/93.7 |
| 2012/0059376 | A1 | 3/2012 | Rains et al. |
| 2013/0039848 | A1 | 2/2013 | Bradbury et al. |
| 2013/0066195 | A1 | 3/2013 | Sirimanne et al. |
| 2013/0230570 | A1 | 9/2013 | Trogler et al. |
| 2014/0017130 | A1 | 1/2014 | Trogler et al. |
| 2014/0187911 | A1 | 7/2014 | Bolan et al. |
| 2014/0243675 | A1 | 8/2014 | Burbank et al. |
| 2015/0057546 | A1 | 2/2015 | Yoon et al. |
| 2015/0143688 | A1 | 5/2015 | Garbini et al. |
| 2015/0173848 | A1 | 6/2015 | Bolan et al. |
| 2015/0273061 | A1 | 10/2015 | Trogler et al. |
| 2016/0051337 | A1 | 2/2016 | Bolan et al. |
| 2016/0143624 | A1 | 5/2016 | Liberman et al. |
| 2016/0151124 | A1 | 6/2016 | Domb et al. |
| 2016/0346404 | A1 | 12/2016 | Trogler et al. |
| 2017/0066162 | A9 | 3/2017 | Fisher |
| 2017/0209601 | A1 | 7/2017 | Kumar et al. |
| 2017/0368209 | A1 | 12/2017 | Alqathami |
| 2018/0021102 | A1 | 1/2018 | Azizian et al. |
| 2018/0065859 | A1 | 3/2018 | Kummel et al. |
| 2018/0092987 | A1 | 4/2018 | Trogler et al. |
| 2018/0280111 | A1 | 10/2018 | Parish |
| 2018/0289444 | A1 | 10/2018 | Blair et al. |
| 2019/0176372 | A1 | 6/2019 | Fisher et al. |
| 2019/0192253 | A1 | 6/2019 | Yang et al. |
| 2019/0365345 | A1 | 12/2019 | Byram et al. |

FOREIGN PATENT DOCUMENTS

| | | |
|---|---|---|
| CN | 103803556 A | 5/2014 |
| CN | 104822626 A | 8/2015 |
| CN | 105377243 A | 3/2016 |
| CN | 106529561 A | 3/2017 |
| CN | 107205792 A | 9/2017 |
| CN | 109200013 A | 1/2019 |
| JP | 2013536024 A | 9/2013 |
| JP | 2016505475 A | 2/2016 |
| JP | 2016516729 A | 6/2016 |
| JP | 6898603 B2 | 6/2021 |
| KR | 20150063097 A | 6/2015 |
| TW | 201900117 A | 1/2019 |
| TW | 201923776 A | 6/2019 |
| WO | 0110302 A3 | 8/2001 |
| WO | 2006105353 A2 | 10/2006 |
| WO | 2009023697 A2 | 2/2009 |
| WO | 2012142625 A2 | 10/2012 |
| WO | 2014052911 A1 | 4/2014 |
| WO | 2016149711 A1 | 9/2016 |
| WO | 2018097891 A1 | 5/2018 |
| WO | 2018187594 A2 | 10/2018 |
| WO | 2019067441 A1 | 4/2019 |
| WO | 2019243419 A1 | 12/2019 |

OTHER PUBLICATIONS

Ding, Xuefeng, et al., "A novel approach to the synthesis of hollow silica nanoparticles," Materials Letters 2004, 58(27-28), 3618-3621.

Huang, Chih-Chia, et al., "Shell-by-shell synthesis of multi-shelled mesoporous silica nanospheres for optical imaging and drug delivery", Biomaterials, 32, 556-564,. (Year: 2011).

Jin, Pu, et al., "Synthesis and catalytic properties of nickel-silica composite hollow nanospheres." J Phys Chem B. May 1, 2004;108(20):6311-4. doi: 10.1021/jp049754g.

Kato, Noritaka, et al., "Synthesis of monodisperse mesoporous silica hollow microcapsules and their release of loaded materials." Langmuir. Sep. 7, 2010;26(17):14334-44. doi: 10.1021/la1024636.

Kempen, Paul J, et al., "Theranostic Mesoporous Silica Nanoparticles Biodegrade after Pro-Survival Drug Delivery and Ultrasound/Magnetic Resonance Imaging of Stem Cells." Theranostics 2015: 5(6) 631-642.

Lee, Jeongwoo, et al., "Synthesis of polystyrene/silica composite particles by soap-free emulsion polymerization using positively charged colloidal silica." J Colloid Interface Sci. Jun. 2007 A181;310(1):112-20. Epub Feb. 15, 2007.

Li, Xin, et al., "Formation of Gold Nanostar-Coated Hollow Mesoporous Silica for Tumor Multimodality Imaging and Photothermal Therapy", 5817-5827, (7), 2017.

Liberman, Alexander, et al., "Color Doppler Ultrasound and gamma imaging of intratumorally injected 500nm iron-silica nanoshells" ACS Nano, Jul. 23, 2013, 7(7) 6367-6377.

Liberman, Alexander, et al., "Hollow iron-silica nanoshells for enhanced high intensity focused ultrasound" J Surg Res, May 10, 2014, 190(2): 391-398.

Liberman, Alexander, et al., "Mechanically tunable hollow silica ultrathin nanoshells for ultrasound contrast agents" Adv Funct Mater, 25(26) 4049-4057, May 21, 2015.

Liu, Jian, et al., "From Hollow Nanosphere to Hollow Microsphere: Mild Buffer Provides Easy Access to Tunable Silica Structure," J. Phys. Chem. C 2008, 112(42), pp. 16445-16451.

Lu, Yu, et al., "Synthesis and crystallization of hybrid spherical colloids composed of polystyrene cores and silica shells," Langmuir, American Chemical Society, 2004, pp. 3464-3470, vol. 20, No. 8.

Mallery, Susan R., et al., Susan R. Mallery et al. Formulation and In-Vitro and In-Vivo Evaluation of a Mucoadhesive Gel Containing Freeze Dried Black Raspberries: Implications for Oral Cancer Chemoprevention, Pharma Res. 24(4), 728-737. (Year: 2007).

Martinez, Paul H, et al., Martinez et al., "Hard shell gas-filled contrast enhancement particles for colour Doppler ultrasound imaging of tumors" Medchemcomm, Oct. 1, 2010(4) 266-270.

Mitchell, et al., "Iron(III)-Doped, Silica Nanoshells: A Biodegradable Form of Silica" J.Am. Chem. Soc. 2012, 34, 13997-14003 (Year: 2021).

Mori, Hideharu, et al., "Organic-Inorganic Nanoassembly Based on Complexation of Cationic Silica Nanoparticles and Weak Anionic Polyelectrolytes in Aqueous and Alcohol Media," Langmuir, vol. 20(5), 2004, pp. 1934-1944.

Nandiyanto, Asep Bayu Dani, et al., "Mesopore-Free Hollow Silica Particles with Controllable Diameter and Shell Thickness Via Additive-Free Synthesis." Langmuir. Jun. 12, 2012;28(23):8616-24. doi: 10.1021/la301457v. Epub May 31, 2012.

Paefgen, Vera, "Evolution of contrast agents for ultrasound imaging and ultrasound-mediated drug delivery," Front Pharmacol 2015, 6, 197.

Parida, Sudam K, et al., "Adsorption of organic molecules on silica surface," Advances in Colloid and Interface Science, 2006, vol. 121, Issue: 1-3, pp. 77-110.

Slowing, Igor I, et al., . "Mesoporous Silica Nanoparticles for Drug Delivery and Biosensing Applications," Adv. Funct. Mater., vol. 17, Issue Apr. 8, 2007 pp. 1225-1236.

(56) References Cited

OTHER PUBLICATIONS

Su, Yang, et al., "Synthesis of hierarchical hollow silica microspheres containing surface nanoparticles employing the quasi-hard template of poly(4-vinylpyridine) microspheres." Langmuir. Jul. 19, 2011;27 (14):8983-9. doi: 10.1021/la2014573. Epub Jun. 23, 2011.
Ta, Casey N., et al., "Integrated processing of contrast pulse sequencing ultrasound imaging for enhanced active contrast of hollow gas filled silica nanoshells and microshells," J. Vac. Sci. Technol. B 30 (2), Mar./Apr. 2012, 6 pages.
Tada, Dayane B, et al., "Methylene Blue-Containing Silica-Coated Magnetic Particles: A Potential Magnetic Carrier for Photodynamic Therapy", Langmuir, 23, 8194-8199. (Year: 2007).
Tissot, Isabelle, et al., "Hybrid Latex Particles Coated with Silica," Macromolecules, Jun. 7, 2001, 34 (17), pp. 5737-5739.
Van Bommel, Kjeld J.C, et al., "Poly(L-lysine) Aggregates as Templates for the Formation of Hollow Silica Spheres," Adv. Mater. vol. 13, Issue 19, Oct. 2001, pp. 1472-1476.
Velikov, Krassimir P, et al., "Synthesis and Characterization of Monodisperse Core-Shell Colloidal Spheres of Zinc Sulfide and Silica," Langmuir, Jul. 10, 2001, 17 (16), pp. 4779-4786.
Voss, R.K., "Doppler Ultrasound-Visible Signal Mark Microspheres are Better Identified than HydroMARK® Clips in a Simulated Intraoperative Setting in Breast and Lung Cancer," Presented at Society of Surgical Oncology meeting Chicago Illinois, Mar. 21-24, 2018.
Wang, H., "Spherical silicon-shell photonic band gap structures fabricated by laser-assisted chemical vapor deposition," J. Appl. Phys. 2007, 101, 033129, Published Online: Feb. 15, 2007 Accepted: Dec. 2006.
Ward, Erin, et al., "Utilization of Iron (III) Doped Nanoshells for in vivo Marking of Non-palpable Tumors using VX2 Rabbit Model." Am. J. Surg., Dec. 2016, 212(6): 1140-1146.
Wu, Dazhen, et al., "Novel One-Step Route for Synthesizing CdS/Polystyrene Nanocomposite Hollow Spheres," Langmuir May 26, 2004, 20, (13), pp. 5192-5195.
Wu, W., et al., "Synthesis of magnetic hollow silica using polystyrene bead as a template." Journal of Magnetism and Magnetic Materials, vol. 311(2), pp. 578-582, available online Sep. 22, 2006.
Xu, Xiangling, et al., "Synthesis and utilization of monodisperse hollow polymeric particles in photonic crystals" J Am Chem Soc. Jun. 4, 2004;126(25):7940-5.
Yao, Hiroshi, et al., "Electrolyte Effects on CdS Nanocrystal Formation in Chelate Polymer Particles: Optical and Distribution Properties", Langmuir 1998, 14(3), 595-601.
Yildirim, Adem, et al., "Stable Encapsulation of Air in Mesoporous Silica Nanoparticles: Fluorocarbon-Free Nanoscale Ultrasound Contrast Agents," Adv Healthc Mater. Jun. 2016; 5(11): 1290-1298.
Zhang, Kun, et al., "Double-scattering/reflection in a Single Nanoparticle for intensified Ultrasound Imaging," Sci Rep, 2015 5:8766.
Zhong, Ziyi, et al., "Preparation of mesoscale hollow spheres of TiO2 and SnO2 by templating against crystalline arrays of polystyrene beads," Adv. Mater. 2000, 12(3), 206-209.
Zhou, W., et al., "Drug-loaded, magnetic, hollow silica nanocomposites for nanomedicine." Nanomedicine: Nanotechnology, Biology and Medicine, vol. 1(3),2005, pp. 233-237.
Zhou, Dejian, et al., "Influence of the Foundation Layer on the Layer-by-Layer Assembly of Poly-L-lysine and Poly (styrenesulfonate) and Its Usage in the Fabrication of 3D Microscale Features." Langmuir, vol. 20(21), 2004, pp. 9089-9094.
Zhu, Yufang, et al., "Stimuli-responsive controlled drug release from a hollow mesoporous silica sphere/polyelectrolyte multilayer core-shell structure," Angew Chem Int Ed Engl. Aug. 12, 2005;44(32): 5083-7.
Chinese Office Action and Search report dated Sep. 25, 2024, for Chinese Application No. 202080093992.0, 15 pages.
Chinese Office Action and Search Report for Chinese Application No. 202080070969.x, with translation, dated Jul. 23, 2024, p. 32.
Chinese Search Report dated Sep. 18, 2024, for Chinese Application No. 2020800948864, 8 pages.
Blair, "Ultrasound Marker Detection, Markers and Associated Systems, Methods and Articles," U.S. Appl. No. 17/003,478, filed Aug. 26, 2020, 51 pages.
CA Office Action Dated: Jun. 17, 2021, Application No. 3,058,898.
EP Search Report mailed Jul. 20, 2023 EP App No. 20857267-1126/4021306 PCT/US2020048023, 10 pages.
European Search Report issued in European Application No. 18781390.2, Mailed Date: Jan. 19, 2021, 8 pages.
Extended EP Search Report mailed Nov. 17, 2022, EP App No. 20891874.8-1122, 7 pages.
Extended European Search Report for 20891745.0, dated Nov. 17, 2022, 8 pages.
Final Office Action mailed Dec. 23, 2022, for U.S. Appl. No. 17/102,761, 22 pages.
First Office Action dated Nov. 9, 2021 for CN201880023936.2, with translation, 24 pages.
Gorsd, Marina N. et al., "Synthesis and characterization of hollow silica spheres", Procedia Material Science, 2015, vol. 8, pp. 567-576.
Huang et al., "Shell-by-shell synthesis of multi-shelled mesoporous silica nanospheres for optical imaging and drug delivery", Chih-Chia Huang et al., Biomaterials, vol. 32, pp. 556-564, (2011).
Hue et al., "Facile synthesis of amino-functionalized hollow silica microspheres and their potential application for ultrasound imaging, He Hu et al," Journal of Colloid and Interface Science, vol. 358, pp. 392-398, 2011.
International Preliminary Report on Patentability dated: Feb. 16, 2010 in International Application No. PCT/US2008/072972 filed: Aug. 13, 2008 and published as: WO 2009/023697 on Feb. 19, 2009, 7 pages.
International Preliminary Report on Patentability dated: Mar. 1, 2016 in International Application No. PCT/US2014/052911 filed: Aug. 27, 2014 and published as: WO 2015/031482 on Mar. 1, 2015, 9 pages.
International Preliminary Report on Patentability dated: Sep. 19, 2017 in International Application No. PCT/US2016/023492 filed: Mar. 21, 2016 and published as: WO 2016/149711 on Sep. 22, 2016, 6 pages.
International Search Report & Written Opinion issued in Application No. PCT/US2020/048023, Mailed Date: Dec. 9, 2020, 17 pages.
International Search Report and Written Opinion dated: Aug. 16, 2016 in International Application No. PCT/US2016/023492 filed: Mar. 21, 2016 and published as: WO 2016/149711 on Sep. 22, 2016, 9 pages.
International Search Report and Written Opinion Dated: Dec. 3, 2018 in International Application No. PCT/US2018/026291 filed: Apr. 5, 2018 and published as: WO/2018/187594 on: Oct. 11, 2018.
International Search Report and Written Opinion dated: Feb. 19, 2009 in International Application No. PCT/US2008/072972 filed: Aug. 13, 2008 and published as: WO 2009/023697 on Feb. 19, 2009, 9 pages.
International Search Report and Written Opinion dated: Oct. 3, 2015 in International Application No. PCT/US2014/052911 filed: Aug. 27, 2014 and published as: WO 2015/031482 on Mar. 5, 2015, 14 pages.
International Search Report and Written Opinion, dated: Apr. 6, 2021 2021, in International Application No. PCT/US2020/062322, 20 pages.
International Search Report and Written Opinion, dated: Mar. 24, 2021, in International Application No. PCT/US2020/062272, 12 pages.
Kamaya et al., Twinkling artifact on color Doppler sonography: dependence on machine parameters and underlying cause, AJR Am J Roentgenol. Jan. 2003; 180(1):215-22. doi: 10.2214/ajr.180.1.1800215. (Year: 2003).
Lu et al., "Synthesis of hollow silica microspheres and their applications in ultrasound imaging", Journal of Shanghai Normal University, vol. 41, Issue 4, pp. 432-439, 2012.
Non Final Office Action for U.S. Appl. No. 17/003,478, mailed Jan. 27, 2022, 28 pages.
Non Final Office Action for U.S. Appl. No. 17/102,758, mailed Dec. 22, 2022, 23 pages.

(56) References Cited

OTHER PUBLICATIONS

Non Final Office Action for U.S. Appl. No. 17/102,761, mailed Jun. 24, 2022, 20 pages.
Notice of Allowance for U.S. Appl. No. 17/102,758, mailed Oct. 12, 2023, 12 pages.
Notice of Reasons for Refusal. Japanese Application No. 2022-530998, dated Oct. 26, 2023, 8 pages.
Notice of Reasons for Rejection, issued in corresponding Japanese Application No. 2021-063419, dated Apr. 11, 2022, 4 pages (English Translation).
Office Action issued in Japanese Patent Application No. 2019-555229, Mailed Date: Dec. 24, 2020, 8 pages.
Office Action issued in Taiwan Application No. 109129539, mailed Mar. 1, 2024, 5 pages.
Office Action issued in Taiwan Application No. 109129539, mailed Oct. 11, 2023, 6 pages.
Richard Barr et al: "Artifacts in diagnostic ultrasound", Reports in Medical Imaging, Jun. 1, 2013, p. 29, XP0555514374, DOI: 10.2147/RMI.S33464, pp. 41-42.
Arnal, Pablo M, et al., "High-temperature-stable catalysts by hollow sphere encapsulation," Angew Chem Int Ed Engl. Dec. 4, 2006;45(48):8224-7.
Brinker, C.J., "Hydrolysis and Condensation of Silicates: Effects on Structure", Journal of Non-Crystalline Solids, vol. 100, 1988, pp. 31-50.
Bunker, Christopher E, et al., "Low-Temperature Stability and High-Temperature Reactivity of Iron-Based Core-Shell Nanoparticles", J. Am. Chem. Soc., 2004, vol. 126, No. 35, pp. 10852-10853.
Caruntu, Daniela, et al., "Synthesis of Variable-Sized Nanocrystals of Fe304 with High Surface Reactivity." Chemistry of Materials, vol. 16(25), pp. 5527-5534. (Year: 2004).
Caruso, Frank, et al., "Electrostatic Self-Assembly of Silica Nanoparticle-Polyelectrolyte Multilayers on Polystyrene Latex Particles," J. Am. Chem. Soc., 1998, 120 (33), pp. 8523-8524.
Caruso, Frank, et al., "Magnetic Nanocomposite Particles and Hollow Spheres constructed by a Sequential Layering Approach." Chemistry of Materials, vol. 13, pp. 109-116. (Year: 2001).
Caruso, Frank, et al., "Nanoengineering of Inorganic and Hybrid Hollow Spheres by Colloidal Templating," Science Nov. 6, 1998: vol. 282, Issue 5391, pp. 1111-1114.
Cha, Jennifer N, et al., "Biomimetic synthesis of ordered silica structures mediated by block copolypeptides", Nature, vol. 403, Issue 6767, pp. 289-292 (2000).

* cited by examiner

MULTI-MODE IMAGING MARKERS

RELATED APPLICATIONS

This application is a continuation of U.S. application Ser. No. 17/473,820, filed Sep. 13, 2021, which is a continuation of U.S. application Ser. No. 15/946,479, filed Apr. 5, 2018 (now U.S. Pat. No. 11,116,599), which claims the benefit of U.S. Provisional Application No. 62/483,274, filed Apr. 7, 2017, and U.S. Provisional Patent Application No. 62/645,677, filed Mar. 20, 2018, each of which are incorporated by reference herein in their entirety.

BACKGROUND

The ability to identify, locate and mark features within the body of a patient has many useful indications. Identifying a specific area within a patient's body with a marker that may be imaged at a later time may be useful for a variety of purposes including observation of that marked area over time, location of a tumor or other type of tissue lesion or abnormality for subsequent study or removal of the tissue lesion as well as other purposes. In certain clinical settings, difficulties may arise where a tissue lesion of interest is most efficiently imaged and marked using a first imaging modality, but subsequent intervention such as surgical removal of the tissue lesion is best accomplished using a second imaging modality or the subsequent intervention that occurs after a substantial passage of time. Other difficulties may arise when the imaging modality available for a particular clinical procedure is not compatible with the type of tissue being imaged such as with the use of ultrasound imaging of lung tissue which is porous with a high density of air to tissue interfaces that interfere with ultrasound energy propagation. What has been needed is imaging markers that are useful for marking a location of interest in a patient's body using multiple imaging modalities. What has also been needed is imaging markers that are stable in location and functional integrity over a suitable time period.

SUMMARY

Some embodiments of a silica shell for multi-mode imaging may include a shell body having a first inner layer which is formed from silica and a second layer which is formed from silica, which is disposed on an outside surface of the first inner layer, and which includes an imaging material configured for producing an imaging signal which is distinct from surrounding tissue. The silica shell also includes a hollow void disposed within an inner surface of the first inner layer. For some embodiments, the silica shell may also include a hydrophobic polymer coating disposed on an outer surface of the second layer.

Some embodiments of a method of manufacturing a silica shell for multi-mode imaging may include forming a first inner layer from silica over a template, removing the template by calcination and applying a second layer of silica which is mixed with an imaging material onto an outer surface of the first layer. Such method embodiments my further include applying a hydrophobic polymer coating onto an outer surface of the second layer.

Some embodiments of a multi-mode composite gel marker for ultrasound imaging may include a plurality of silica shells, each silica shell including a shell body having a layer which is formed from silica and a hollow void disposed within an inner surface of the layer which is formed from silica. The composite gel marker may also include an imaging material which is configured to produce an imaging signal that is distinct from surrounding tissue and a hydroscopic gel material which is disposed about the plurality of silica shells and imaging material so as to form an expandable gel marker body. For some embodiments of such a multi-mode composite gel marker, the plurality of silica shells may include a shell body having a first inner layer which is formed from silica and a second layer which is formed from silica, which is disposed on an outside surface of the first inner layer, and which includes the imaging material configured for producing an imaging signal which is distinct from surrounding tissue. The silica shells also include a hollow void disposed within an inner surface of the first inner layer. In some cases, a hydrophobic polymer coating may be disposed on an outer surface of the second layer of the plurality of silica shells.

Some embodiments of an applicator for delivering a multi-mode composite gel marker to a target site within subdermal tissue of a patient may include a handle having an interior cavity, a slide bore and a retraction slot. The applicator may also include a cannula having an inner lumen extending a length thereof and a positioning rod which is disposed within the inner lumen of the cannula and which has a proximal end secured to the handle. The applicator may also have a retraction shuttle which is secured to a proximal end of the cannula, which includes a lumen that is coaxial with the inner lumen of the cannula and which slides within the slide bore of the handle thereby imparting relative axial displacement between the cannula and the positioning rod. The applicator may also include a retraction knob which is secured to the retraction shuttle and which is disposed within the retraction slot of the handle in a distal axial position such that the retraction slot mechanically limits the axial movement of the retraction knob and cannula between the distal axial position with a distal end of the cannula extending distally beyond a distal end of the positioning rod and a proximal axial position with the distal end of the cannula being disposed proximal of the distal end of the positioning rod. A composite gel marker in an unexpanded state may be disposed in a cavity formed within the inner lumen of the cannula between the distal end of the cannula and the distal end of the positioning rod with the retraction knob and cannula in the distal axial position.

In some instances, the applicator may also include an interlock which has a first tab secured to and extending inwardly from an inner surface of the interior cavity of the handle and a second tab extending outwardly from the retraction shuttle. The second tab may be in an overlapped configuration with respect to the first tab along a direction substantially parallel to a longitudinal axis of the positioning rod and cannula such that proximal retraction of the retraction knob while in the distal axial position is mechanically prevented by the overlapped configuration of the first tab and second tab until the retraction knob is depressed so as to eliminate the overlap between the first tab and second tab. For some embodiments, such applicators may also have a removable interlock including a removable block having a snap fit into the retraction slot proximal of the retraction knob when the retraction knob is in a distal axial position. This configuration serves to mechanically prevent proximal retraction of the retraction knob until the removable interlock is manually removed from the retraction slot.

Some methods of marking and ultrasound imaging a target site within a patient's body may include advancing a distal end of a cannula of an applicator to a target site within a patient's body below a surface of the patient's skin. The distal end of the cannula may be advanced such that a multi-mode composite gel marker disposed within a cavity in an inner lumen of the cannula between a distal end of the cannula and a distal end of a positioning rod disposed within the inner lumen of the cannula is in a desired position relative to the target site. Such methods may also include proximally retracting a retraction knob and the cannula of the applicator relative to tissue of the target site, the composite gel marker, the positioning rod and a handle of the applicator until the outer radial constraint of an inner surface of an inner lumen of the cannula is removed from the composite gel marker so as to deploy the composite gel marker at the target site. Thereafter, the cannula and positioning rod may be withdrawn from the patient's body. The composite gel marker and adjacent target site may subsequently be imaged with ultrasound imaging.

Some methods of marking and ultrasound imaging a target site disposed within lung tissue of a patient's body may include deploying a composite gel marker at a target site within lung tissue of the patient with the composite gel marker extending from the target site to an outer surface level of the patient's lung. Thereafter, the target site may be imaged with ultrasound from the outer surface level of the patient's lung through the marker and to the target site with an ultrasound imaging signal that travels through the composite gel marker from the outer surface level to the target site.

Certain embodiments are described further in the following description, examples, claims and drawings. These features of embodiments will become more apparent from the following detailed description when taken in conjunction with the accompanying exemplary drawings.

The drawings are intended to illustrate certain exemplary embodiments and are not limiting. For clarity and ease of illustration, the drawings may not be made to scale and, in some instances, various aspects may be shown exaggerated or enlarged to facilitate an understanding of particular embodiments.

DETAILED DESCRIPTION

As discussed above, the ability to identify, locate and mark features within the body of a patient has many useful indications. Identifying a specific area within a patient's body with a marker that may be imaged at a later time may be useful for a variety of purposes including observation of that marked area over time, location of a tumor or other type of tissue lesion or abnormality for subsequent study, removal or other type of treatment such as ablation or adjuvant therapy as well as other purposes. In certain clinical settings, difficulties may arise where a tissue lesion of interest is most efficiently imaged and marked using a first imaging modality, but surgical removal of the tissue lesion is best accomplished using a second imaging modality. In such cases, a marker embodiment that is stable in position and over time after deployment and that can be imaged by at least two distinct imaging modalities may be useful.

Figure 1:
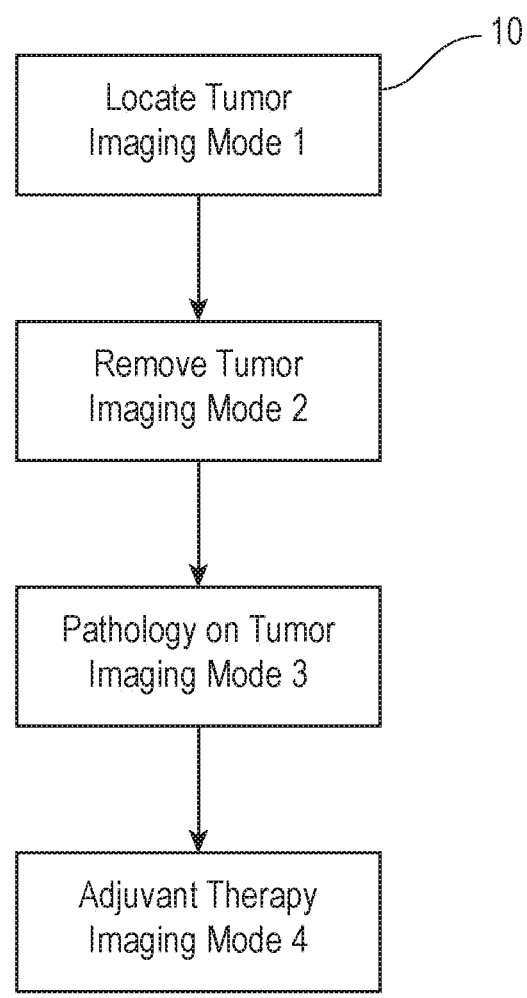
FIG. 1 is a flow chart directed to a general process of multi-mode imaging during surgical removal of a tumor.

For example, it may be preferred for a tissue lesion to be imaged and marked under fluoroscopy, computed tomography (CT) imaging, or MRI, by a specialist such as a radiologist. The marker used to identify the location of the tissue lesion that is deployed by the radiologist under fluoroscopy, for example, must therefore be suitable for imaging under corresponding fluoroscopy to facilitate deployment of that marker. Subsequent to that deployment by the radiologist, a different type of imaging may be used to facilitate the subsequent therapeutic procedure, possibly during surgical removal or other type of treatment of the tissue lesion. For example, visual imaging with direct viewing of the marker with the eyes of a surgeon and/or ultrasound imaging, including color flow Doppler ultrasound imaging may be used during such a surgical procedure. In the case of directly viewing the marker, the marker embodiment must be visually distinct from surrounding tissue for visual imaging. In the case of ultrasound imaging, the marker must reflect an ultrasound signal that is distinct from an ultrasound signal reflected from surrounding tissue. Furthermore, in some cases, it may be useful to use the second, third or a fourth type of imaging to evaluate excised tissue after surgical removal from the patient or for any other suitable indication. See the flowchart 10 shown in FIG. 1 as an example of this type multi-mode imaging and corresponding diagnostic and therapeutic procedures. For such cases, the marker or portions thereof may be disposed within the excised tissue and again facilitate location of the tumor or other abnormal tissue within the excised tissue during post procedure analysis. In addition, if some markers remain at the site of the lesion, these may be used as fiducials for adjuvant therapy and the like.

Figure 2:
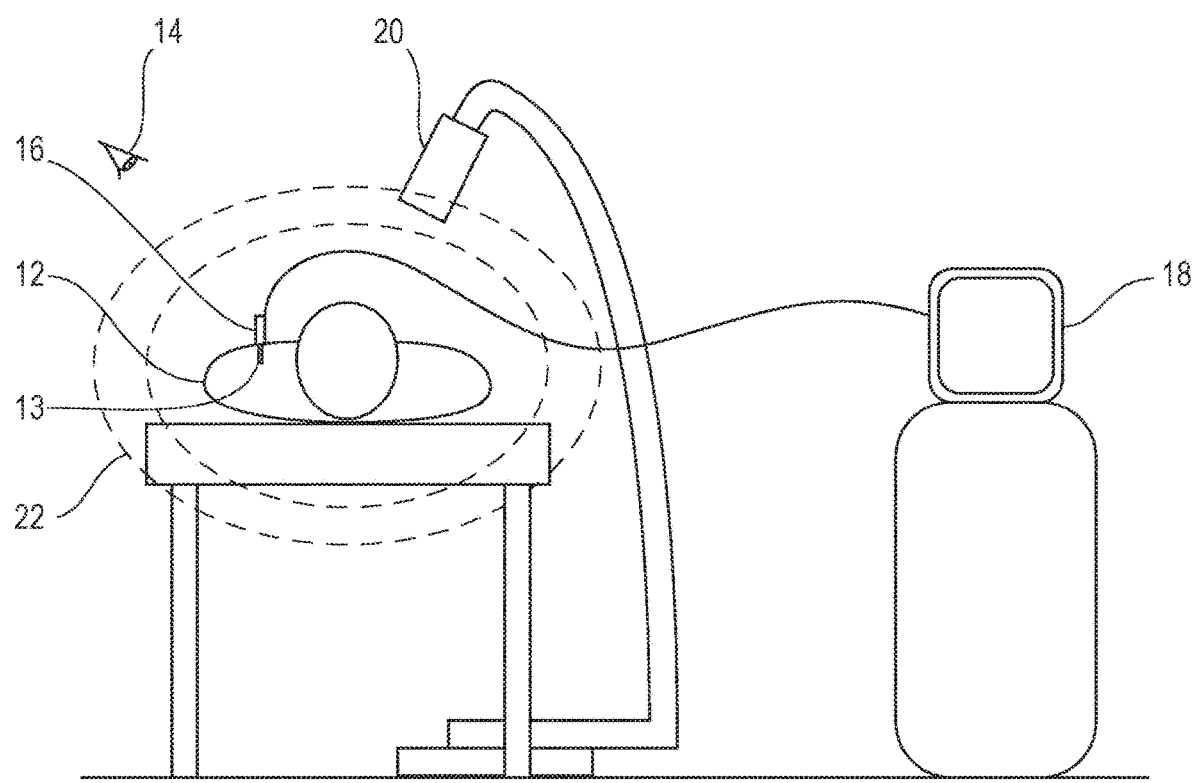
FIG. 2 is as schematic view of a patient lying on a table and being imaged by a plurality of imaging modalities.

FIG. 2 is a schematic representation of a patient's body tissue being imaged by a plurality of imaging modalities including four different modalities. In particular, the patient's body 12 and marker 13 (which may include any of the marker embodiments discussed herein) are being imaged visually by direct observation through the eyes 14 of an observer. Such visual observation may also include camera imaging such as might be used by a robotic surgery device or microscopy that might be used during surgery or at pathology or any other suitable use. Certain audio imaging may also be useful in some circumstances. The patient's body 12 and marker 13 shown in FIG. 2 are also being imaged with ultrasound using an ultrasonic probe 16 and monitor 18, with fluoroscopy using a c-arm type unit 20 and with MRI with a dashed outline indicating a magnet 22 of an MRI apparatus and the remainder of the MRI apparatus not shown for purposes of clarity. Although the patient 12 and marker 13 are shown in FIG. 2 being imaged by four different imaging modalities at the same time, any or each of these imaging modalities may be carried out at different times and at different locations. In addition, the patient 12 and marker 13 could further be imaged by any other suitable imaging modality at the same time or different times.

Unless otherwise indicated, use of the term imaged or imaging of a marker 13 herein refers to recognition of a return signal from a marker embodiment that is distinct from a return signal of tissue (or other material) surrounding or adjacent to the marker. For example, direct visual imaging of a marker embodiment 13 may include the ability of an observer to see the marker embodiment 13 relative to the surrounding tissue due to a difference in color (for example) between the marker embodiment 13 and the surrounding tissue. A marker embodiment 13 imaged with ultrasound may reflect an ultrasound signal that is distinct in intensity, wavelength, phase etc. relative to an ultrasound signal reflected by tissue surrounding or adjacent such a marker embodiment 13. In addition, effective imaging in many cases does not need to include image projection onto a display screen for viewing by an operator such as is typically the case with fluoroscopic, ultrasonic and magnetic resonance imaging (MRI). Imaging of a marker embodiment 13 may include reflection or return of some type of an energetic signal by the marker embodiment 13 that may be projected from multiple points of origin in order to specify the location of a marker embodiment in three-dimensional space by methods such as triangulation. Such a technique may provide location information of the marker embodiment 13 relative to the position of the multiple points of origin of the energetic signal. With regard to audio imaging, an audible sound may be configured to increase in pitch, intensity, frequency or the like as a function of a probe's proximity to a marker and/or such a probe's appropriate directionality with respect to a marker 13.

For certain indications, it may be desirable to use certain types of imaging modalities. In many cases, imaging modalities such as direct visual observation and ultrasound imaging may be desirable over other imaging modalities because they do not subject the patient or attending clinicians to high energy electromagnetic radiation and they are convenient and relatively inexpensive to use. FIGS. 3-9 illustrate the construction of a silica shell 24 that includes the addition of a dye to such a small silica shell structure that allows a suitable number of such dyed silica spheres to be visualized with the naked eye as well as providing a strong ultrasound imaging signature due to the hollow nature of the silica shell 24 as well as other properties that enhance the ultrasonic signature.

Some embodiments of a silica shell 24 for multi-mode imaging may include a shell body 26 having a first inner layer 28 which is formed from silica and a second layer 30 which is formed from silica, which is disposed on an outside surface 32 of the first inner layer 28, and which includes an imaging material 29 configured for producing an imaging signal which is distinct from surrounding tissue. The silica shell 24 also includes a hollow void 34 disposed within an inner surface of the first inner layer. For some embodiments, the silica shell 24 may also include a hydrophobic polymer coating 36 disposed on an outer surface 38 of the second layer 30. Embodiments of suitable imaging materials 29 may include a wide variety of materials suitable for specifically generating a distinct return signal for a variety of corresponding imaging modalities including direct visual observation, ultrasound imaging, fluoroscopy, MRI and the like.

These small silica shell embodiments 24 which may have a spherical configuration in some cases may be useful for multi-mode imaging indications that utilize direct visual observation, ultrasound imaging, or both of these modalities. Some composite gel marker embodiments 40 (discussed below) may include hollow silica shells 24 that have a distinct signal on Doppler ultrasound imaging. In some cases, tumors injected with such silica shells 24 have been excised with significantly less marker migration relative to traditional wire localization. Some such silica shell embodiments 24 may be identified intraoperatively with color Doppler ultrasound imaging and B-mode ultrasound imaging in an intraoperative setting.

Under B-mode ultrasound imaging, some composite gel marker embodiments discussed herein may appear similar to other commercially available ultrasound markers. However, in some cases, under Doppler mode, some of the composite gel marker embodiments that include hollow silica shells 24 and discussed herein may generate a robust, highly-colored signal. Composite gel marker embodiments 40 discussed herein that are visible under standard B-mode ultrasound may appear with an imaging signature that is similar to the imaging signature or reflected signal of previously available imaging markers, however, these same composite gel markers 40 that include hollow silica shell embodiments 24 and the like may also emit a colorful signal under Doppler ultrasound allow for rapid identification with any standard ultrasound machine. Furthermore, some composite gel marker embodiments 40 discussed herein may be visible at any depth that can be imaged with ultrasound. Some gel marker embodiments 40 discussed herein may also appear on a surface of the lung as a blue-gray mark that may be distinct in appearance from surrounding lung tissue to further facilitate location of such composite gel markers 40.

Figure 3:
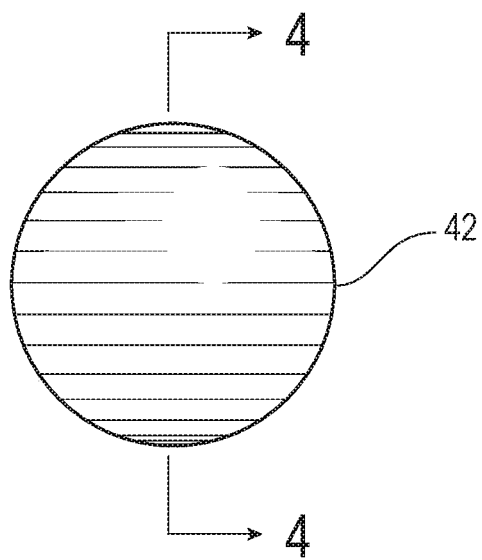
FIG. 3 is an elevation view of a spherical template embodiment for production of a hollow spherical structure.
Figure 4:
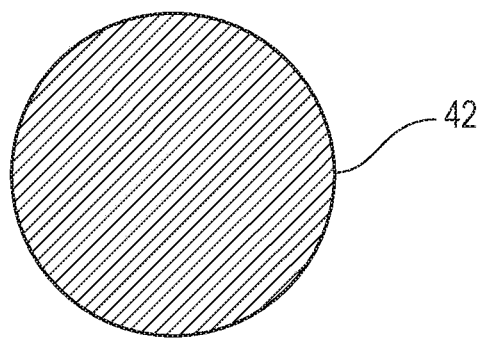
FIG. 4 is a cross section of the template embodiment of FIG. 3.

Some embodiments of a method of manufacturing a silica shell for multi-mode imaging may include forming a first inner layer 28 from silica over a template 42, removing the template 42 by calcination and applying a second layer of silica 30 which is mixed with an imaging material 29 onto an outer surface 32 of the first layer 28. Such method embodiments my further include applying a hydrophobic polymer coating 36 onto an outer surface 38 of the second layer 30. FIG. 3 shows an polystyrene bead that may serve as a template 42 for formation of silica shell embodiments 24. In some cases, the polystyrene bead 42 may have a spherical configuration and a diameter of about 1.8 microns to about 2.2 microns which may produce a silica shell 24 having an outer transverse dimension, in some cases an outer diameter, of about 1.8 microns to about 2.2 microns. However, embodiments with different shapes and other sizes may be suitable in some cases. For example, such silica shells 24 having diameters of about 50 nm, 100 nm, 200 nm, 350 nm as well as other sizes including larger sizes have been shown to produce a strongly reflective and distinct ultrasound signature and return signal that is distinct from surrounding tissue and may be used for any of the marker embodiments, including composite gel marker embodiments 40, discussed herein. Some such silica shell embodiments 24 which are useful for ultrasound imaging and use in composite gel markers 40 or the like may have an outer transverse dimension or diameter of about 50 nm to about 20 microns, more specifically, about 100 nm to about 2.2 microns, and even more specifically, about 200 nm to about 1.8 microns.

Figure 5:
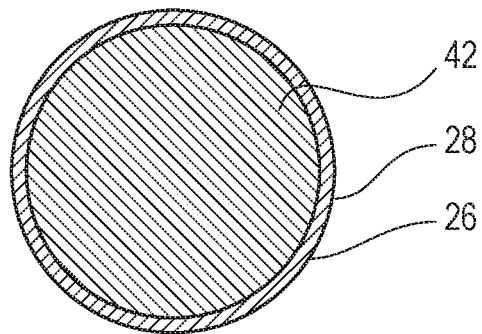
FIG. 5 is a cross section of the template embodiment of FIG. 3 with an embodiment of a layer of silica particles disposed thereon with the layer of silica particles forming a spherical silica shell.
Figure 10:
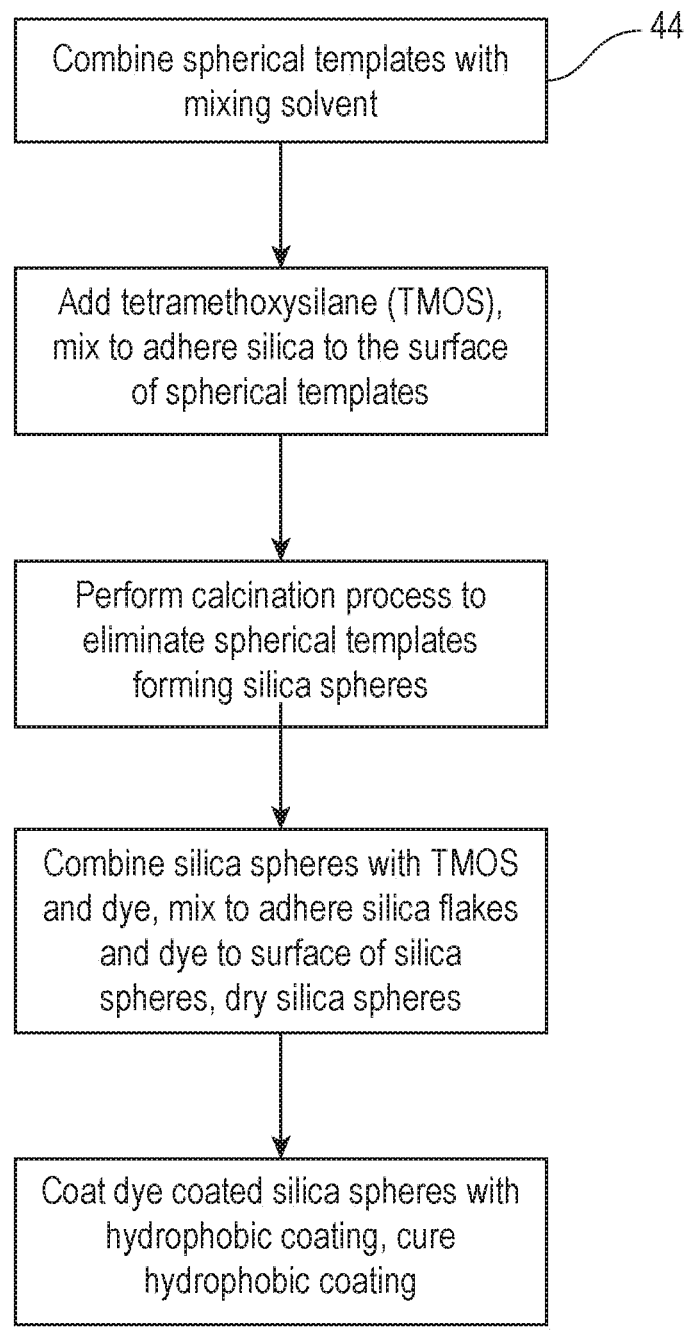
FIG. 10 is a flow chart directed to a method of making a silica shell embodiment as shown in FIG. 8.

For some embodiments the polystyrene bead 42 may be made by Polyscience Co. Part No. 19814-15. In general, a method for making hollow silica shells 24 as shown in the flow chart 44 of FIG. 10 may include combining a plurality of the polystyrene template beads 42 with a mixing solvent such as 95% ethanol, adding tetramethoxysilane (TMOS) to the solvent, mixing the components under high shear for an extended time, such as about 4-6 hour in some cases, to produce silica particles which are adhered to the polystyrene templates 42 as shown in FIG. 5.

Figure 6:
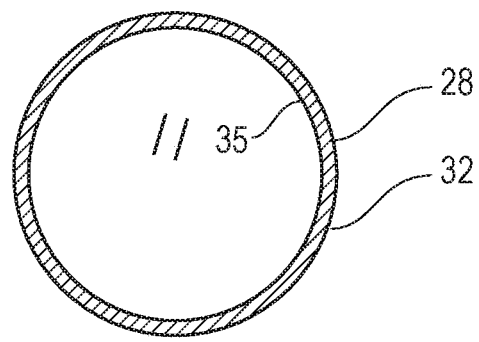
FIG. 6 is a cross section of the silica shell embodiment of FIG. 5 with the spherical template removed from within an interior volume of the silica shell.
Figure 7:
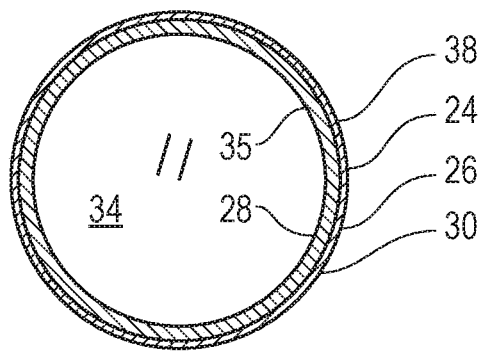
FIG. 7 is a cross section of the silica shell embodiment of FIG. 6 with an embodiment of a second layer of silica particles combined with a visually distinct dye disposed on an outer surface of the silica shell of FIG. 6.

A calcination process is then performed at temperatures of about 530° C. to about 570° C. for about 5 hours in order to remove the polystyrene templates 42 from the center of the silica shells 24 to form hollow silica spheres as shown in FIG. 6. These newly formed hollow silica shells which include the first layer 28 only at this stage may then be treated as a first inner layer 28 and processed a second time by combining the hollow silica shells 28 with more TMOS, a mixing solvent and an imaging material 29 for direct visual observation such as a visual dye, more specifically such as methylene blue, into a container and again mixing under high shear conditions in order to plate or otherwise add a second layer 30 of silica particles to the pre-existing silica shell 28 first inner layer, the second layer 30 being infused with the imaging material 29 including methylene blue. In some cases, during the second mixing process, the methylene blue may also become infused into the interstices of the first or inner layer 28 of silica particles forming the predicate silica shell as shown in FIG. 7. In some cases the methylene blue is added during a second layer plating process because the methylene blue cannot easily withstand the temperatures of the calcination process used to remove the template 42 from the inner void 34 of the first layer 28.

Figure 8:
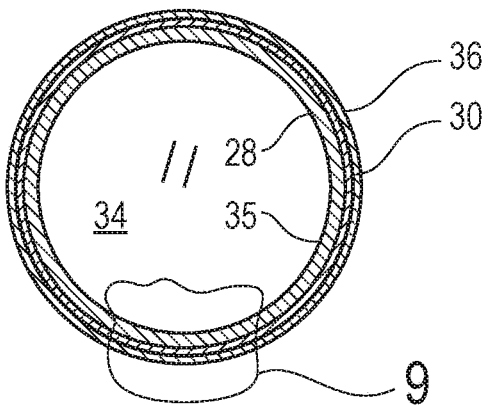
FIG. 8 is a cross section of the silica shell of FIG. 7 with an optional outer layer of hydrophobic polymer coated onto an outer surface of the outer second layer of silica particles and dye.
Figure 9:
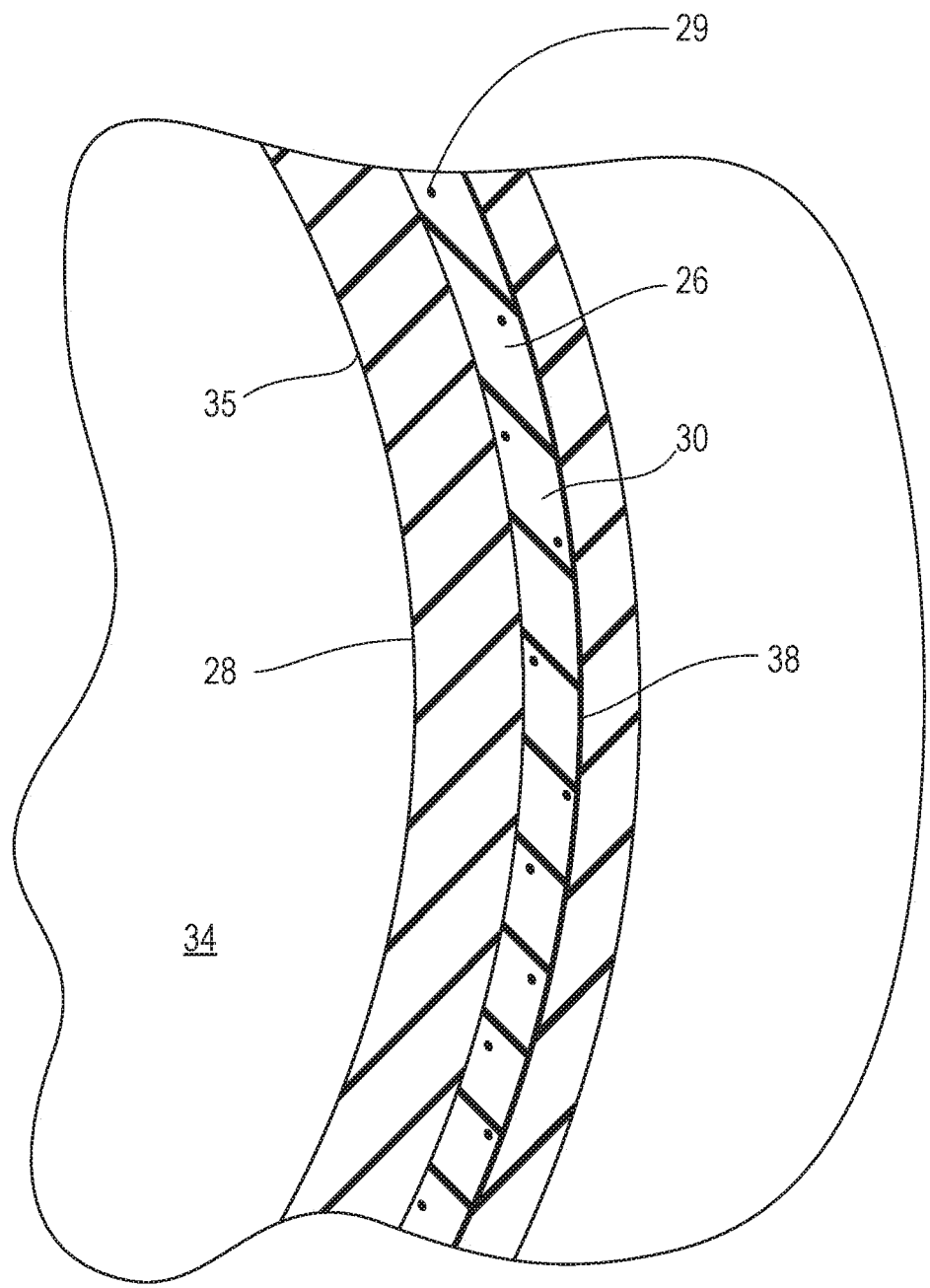
FIG. 9 is an enlarged view of the silica shell structure of FIG. 8 indicated by the outlined portion 9-9 of FIG. 8.

The dyed silica shells 24 may then be dried to drive off any remaining mixing solvent. The dried silica shells 24 are now multi-layer, hollow and the shell material, or portions thereof, infused in methylene blue giving them a distinct blue color which is visible to the naked eye when placed against materials having colors similar to tissue colors typically encountered during a surgical procedure. Thereafter, the silica shells 24 may be coated with the optional hydrophobic polymer coating 36 or any other suitable coating in order to seal the hollow cavity 34 within each silica shell 24 and prevent ingress of fluids such as bodily fluids and the like. Other suitable coatings or configurations that may be used in order to maintain the hollow character of the silica shells 24 when deployed in an in vivo environment may include painting, powder coating, dispersion coating in addition to compounding such hollow silica shells 24 into injection molding or extrusion processes. Such an embodiment of a coated silica shell 24 is shown in FIGS. 8 and 9. In some cases, the silica shells 24 may be coated using a polymer such as octyltriethoxysilane dissolved in a solvent such as ethanol.

Figure 11:
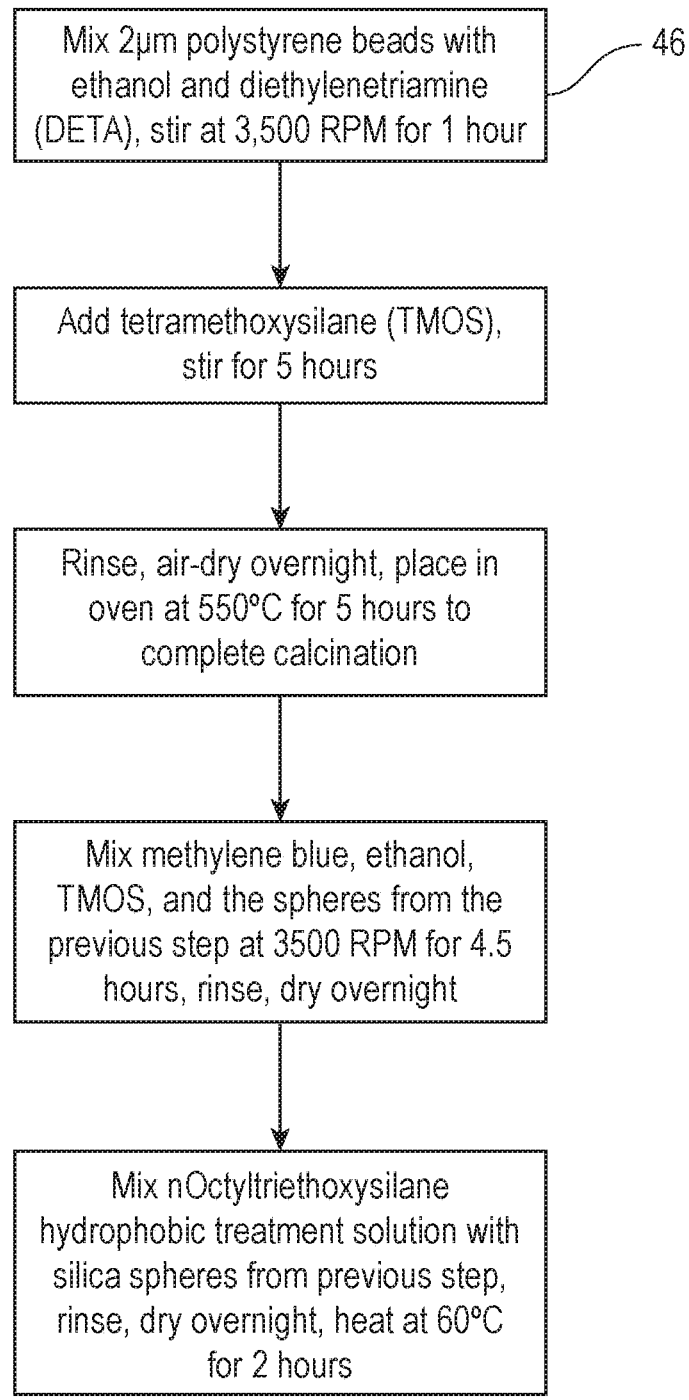
FIG. 11 is a flow chart directed to a method of making a silica shell embodiment as shown in FIG. 8.

The silica shells 24 in this configuration may thus serve as multi-mode imaging markers by providing a distinct visual signal that can be recognized by the naked eye of a human operator (or visual imaging system of a robotic device) as well as providing a strong ultrasound imaging signature for ultrasound imaging including color Doppler imaging. FIG. 11 shows a flowchart 46 that outlines a similar procedure for making silica shells 24 and includes more detail regarding the specific parameters of certain process embodiments. In some cases, it may be possible to further include or substitute other imaging materials 29 into the first layer 28, the second layer 30 or both layers of silica shells 24, their respective interior volumes 34 or outer surfaces 32,38 thereof. For example, imaging materials 29 such as radiopaque materials may be included in the first layer 28 or the second layer 30 of such silica shells 24 to provide an imaging signature under fluoroscopy and the like. MRI imaging materials 29, such as any of those MRI imaging materials discussed herein, may also be so included in the first layer 28 or the second layer 30 of such silica shells 24 to provide an MRI image signature under MRI imaging. It should also be noted that although the silica shell embodiments 24 discussed herein are generally described as being made from silica, the same functionalities and uses discussed herein may be achieved with similar structures that are not made primarily of silica and that vary from a spherical shape but do retain a hollow configuration.

In some cases, for the processes above for making the silica shells 24, it may be desirable to maintain a certain amount of the optional hydrophobic coating on the outer surface 38 of each silica shell 24 in order to ensure the integrity and imaging quality of the silica shells 24, particularly with regard to the color Doppler ultrasound imaging quality of the shells in some cases. Therefore, in some cases, it may be desirable to avoid rinsing the silica shells 24 in a solvent that might dissolve the hydrophobic coating 36 once the optional hydrophobic coating 36 has been applied. For some embodiments, it may be desirable for the finished and dried silica shells 24 to have an optional hydrophobic polymer coating 36 that is about 0.1 percent to about 5.0 percent by weight of the total weight of the silica shells 24 disposed on an outer surface 38 of the second layer 30 of the silica shells 24. In some other cases, the optional hydrophobic coating 36 may not be necessary in order to maintain the integrity imaging quality of the silica shells 24 including for color Doppler ultrasound imaging. In such cases, it may only be desirable to maintain the hollow character of the silica shells 24 by preventing liquid ingress into the interior volume of the silica shells 24. In some cases, an outer hydrophobic polymer coating 36 may be made from octyltriethoxysilane or the like as discussed above.

Some exemplary hollow silica shell embodiments 24, including silica shells having an outer diameter of about 1.8 microns to about 2.2 microns, more specifically, about 2 microns, may be manufactured by mixing about 18 microliters (±1 mg) of (3-trimethoxysilypropyl) diethylenetriamine (DETA) with about 40 ml (±2%) of 100% ethanol alcohol. About 60 ml of polystyrene template beads 42 having an outer diameter of about 2 microns and about 400 g (±1%) of 95% ethanol alcohol may also be added to the DETA/alcohol mixture in a one liter depyrogenated FEP container and stirred at about 3,500 rpm for about an hour. In general, all of the containers used for the following procedures would be depyrogenated in order to maintain a purity of the components being processed and many or all of the following procedures would be carried out in a controlled environment area. Thereafter, about 3.3 ml (3.4534 g±2%) of tetramethoxysilane (TMOS) may be added to the alcohol, DETA and polystyrene template bead 42 mixture and stirring continued for about 4 more hours in order to plate a first inner layer 28 of silica on an outer surface of the polystyrene template beads 42.

The stirred TMOS material may then be transferred into sterile test tubes and centrifuged at about 3,000 rpm for about 30 minutes, after which time the fluid from the centrifuged TMOS mixture may be removed with a sterile syringe or the like and then discarded. The particles which remain in the test tubes may then be rinsed with about 50 ml of 95% ethanol alcohol in each test tube and centrifuged again at about 3,000 rpm for about 30 minutes. This rinsing step may then be repeated two times. It may also be desirable in some cases to transfer the particles from one test tube into another test tube in order to consolidate the particles and reduce the number of test tubes being used after each of the rinse cycles.

The particles may then be transferred to one or more crucibles, such as two 20 ml to 30 ml crucibles, and allowed to air dry overnight under a laminar flow hood or the like. The crucibles containing the particles may then be transferred into an oven and the temperature in the oven ramped up at about 2 degrees centigrade per minute to a temperature of about 550 degrees centigrade. The particles in the crucible may thereafter be maintained at the temperature of about 550 degrees centigrade for about 5 hours in order to calcinate the particle structure and remove the polystyrene template bead 42 from the interior cavity 34 of the particles leaving a hollow silica shell structure 28. The silica shells 28 may thereafter be allowed to cool and then be broken apart from each other with a depyrogenated steel spatula or the like.

For a second layer of material 30 to be plated to the calcinated hollow silica shells 28, about 6 g of methylene blue 29 may be mixed at about 6,000 rpm for about one hour with about 500 ml (400 g±1%) of 95% ethanol alcohol and then filtered. This methylene blue mixture may then be transferred to 50 ml test tubes and centrifuged for about ten minutes at about 3,000 rpm. Once again, about 18 microliters of DETA may be mixed with about 40 ml (31.3 g±2%) of 95% ethanol alcohol in a 50 ml test tube which may in turn be added to the alcohol and methylene blue mixture of the previous step in an FEP container. The calcinated hollow silica shells 28 may also be added to this alcohol, DETA and methylene blue mixture and the entire mixture may then be stirred at about 3,500 rpm for about 1 hour. At about 1 hour, about 3.3 ml (3.4534 g±2%) of TMOS may be added and stirring continued for about 3.5 more hours to allow for dying and shell plating onto the originally produced silica shells 28.

Once again, this material may then be transferred into 50 ml test tubes and centrifuged at about 3,000 rpm for about 30 minutes, after which time the fluid from the centrifuged TMOS and methylene blue mixture may be removed with a sterile syringe and then discarded. The silica shells 24 which remain in the test tubes may then be rinsed with about 20 ml to about 30 ml of 95% ethanol alcohol and centrifuged again at about 3,000 rpm for about 30 minutes. This rinsing step may then be repeated two more times reducing the number of test tubes after each rinse in order to consolidate the silica shells 24 and reduce the number of test tubes as discussed above. The shells may then be transferred to one or more crucibles and allowed to air dry overnight under a laminar flow hood or the like.

A hydrophobic outer layer solution may then be prepared by mixing about 100 microliters (90 mg±2%) of octyltriethoxysilane with about 10 ml (7.6957 g±2%) of 100% ethanol alcohol in a vortex mixer for about 30 seconds. The two-layer hollow silica shells 24 may then be added to this mixture and mixed with a spatula or the like in order to create a homogeneous suspension. The silica shells 24 may be soaked in this mixture and allowed to dry overnight in order to apply a hydrophobic outer layer 36 to the silica shells 24. The silica shells 24 may then be transferred to a 50 ml test tube and rinsed one time in 95% ethanol alcohol and centrifuged at about 3,000 rpm for about 30 minutes and thereafter discarding the fluid. This rinsing, centrifuging and discarding of the rinsing fluid step may be repeated two more times. The thrice rinsed two-layer hollow silica shells 24 may then be transferred to one or more crucibles and allowed to air dry overnight under a laminar flow hood or the like.

The dried silica shells 24 may then again be rinsed in 95% ethanol alcohol and centrifuged again and allowed to dry overnight again. The crucibles and silica shells disposed therein may then be heated in a stable oven at about 60 degrees centigrade for about two hours. The resulting two-layer hollow silica shells 24 may then be measured and observed in order to verify the production process and quality of the silica shells 24. In some cases, the polystyrene template beads 42 used for such a process may include part number 19814-15 manufactured by the Polysciences Company, the DETA may include part number SIT8398.0 manufactured by the Gelest Company, the TMOS may include part number T2033 manufactured by the Spectrum Company, the octyltriethoxysilane may include part number 01472 manufactured by the Spectrum Company and the methylene blue may include part number J60823 manufactured by the Alfa Aesar Company.

In some cases, the two-layer hollow silica shells 24 produced by the plating process discussed above may be further processed into a composite gel marker 40 as generally shown in FIGS. 12-15 for use in testing of the silica shells 24, testing of the composite gel marker 40 or clinical use in marking a site associated with a patient's body 12. In some cases, a functionality test sample may be manufactured by combining the hollow silica shells 24 manufactured by the process above with a gel material 48 such as chitosan, and more specifically, processed chitosan 70/2000. For such a sample, a mixture of about 2 mg of hollow silica two-layer shells 24 to about 1 ml of chitosan 48 may be injected into several silicone tubes 50 having an inner lumen diameter of about 2.3 mm to about 2.5 mm. The tubes 50 may then be frozen and subsequently freeze dried with a sodium hydroxide solution including about 25 ml of sodium hydroxide mixed with about 100 ml of distilled water. Such freeze dried gel marker embodiments 40 may then be removed from the silicone tubes 50 and used for testing, clinical use, or any other suitable purpose. In some cases, such gel marker embodiments 40 may be able to hydrate rapidly, achieving full hydration when disposed within an aqueous environment within 24 hours in some cases. Such gel marker embodiments 40 may be sized and configured to fit into a 20 gauge syringe applicator device with sufficient interference for an accurate and timely deployment. Such gel marker embodiments 40 may also be configured to serve as an external acutely visible lung tissue marker with minimal migration in tissue, be visible using color Doppler ultrasound imaging systems 24 hours or more after injection and maintain ultrasound visibility for about 2 weeks or more.

Various embodiments of silica shells which may include silica nanospheres and silica microspheres are discussed herein. Further details regarding the manufacture and properties of various nanosphere and microsphere embodiments are discussed in PCT Publication No. WO 2009/023697, filed Aug. 13, 2008, by The Regents of the University of California, titled "Hollow Silica Nanospheres and Methods of Making Same, published Feb. 19, 2009, and PCT Publication No. WO2014/052911, filed Sep. 27, 2013, by The Regents of the University of California, titled "Degradable Silica Nanoshells for Ultrasonic Imaging/Therapy", published Apr. 3, 2014, and PCT Publication No. WO 2016/149711, filed Mar. 21, 2016, by The Regents of the University of California, titled "Silica Nanostructures, "Large-Scale Fabrication Methods, and Applications Thereof", published Sep. 22, 2016, all of which are incorporated by reference herein in their entirety.

Once these silica shell embodiments 24 discussed above have been made, they are functional as multi-mode imaging markers 13 and may be used for imaging in a variety of conditions and in a variety of configurations. The silica shell embodiments 24 discussed herein by themselves may be useful for a wide variety of indications that involve observation and/or measurement of internal bodily processes and the distribution of certain tissue or fluid types within a patient's body 12. For example, silica shells 24 which are capable of being imaged with color flow Doppler ultrasound may be introduced into a patient's body 12 by direct deployment into tissue, systemic injection into the bloodstream, lymph system etc. or any other suitable method. The dispersion of the two-layer silica shells 24 may then be observed, for example, by color flow Doppler imaging. In some cases, it has been discovered that it may be possible to measure a concentration of silica shell embodiments 24 within a volume of tissue or fluid within a patient's body 12 by performing a pixel count analysis of the image data produced by the color Doppler imaging. As such, once such silica shells 24 have been introduced into the patient's body 12, a desired location within the patient's body 12 may be imaged using color flow Doppler ultrasound. A pixel count analysis may then be performed on the image data collected by the color Doppler ultrasound process and a concentration level of the silica shells 24 determined for a given volume of the tissue or fluid imaged. Such a method may be used to image a tumor within the tissue of a patient and measure a concentration of silica shells 24 that have been absorbed by the tumor as well as locating the position of the tumor or other type of tissue lesion.

Figure 12:
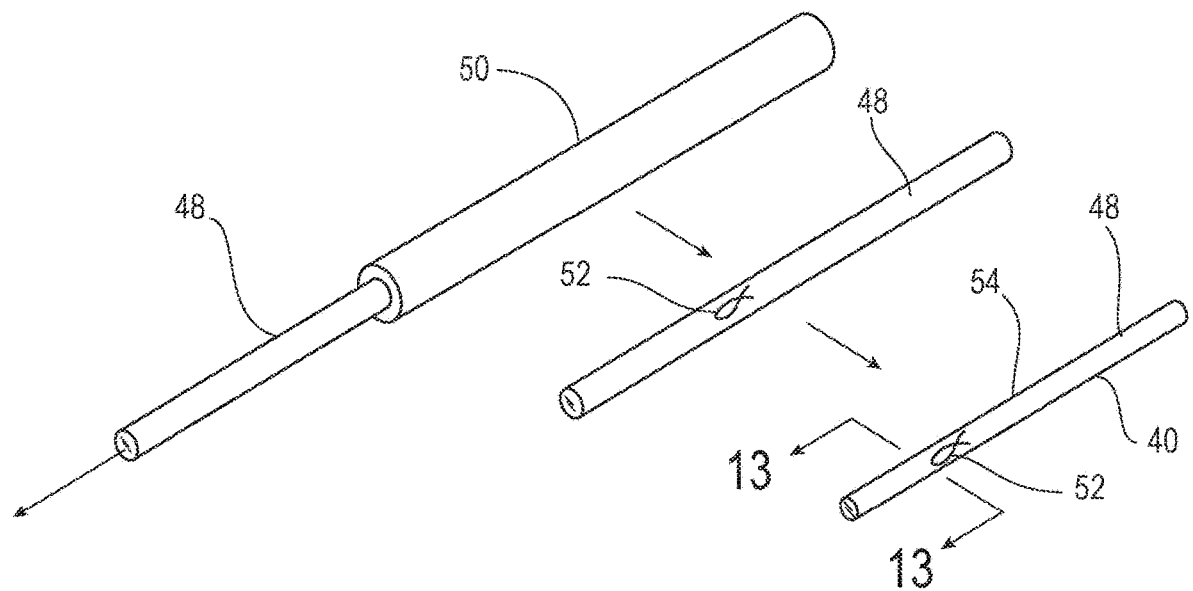
FIG. 12 is a perspective view of a molding method for making a composite gel marker embodiment that includes a plurality of the silica shells of FIG. 8 as well as well as at least one other marker embodiment molded together in substantially fixed relation to each other with an expandable hydrophilic gel.
Figure 13:
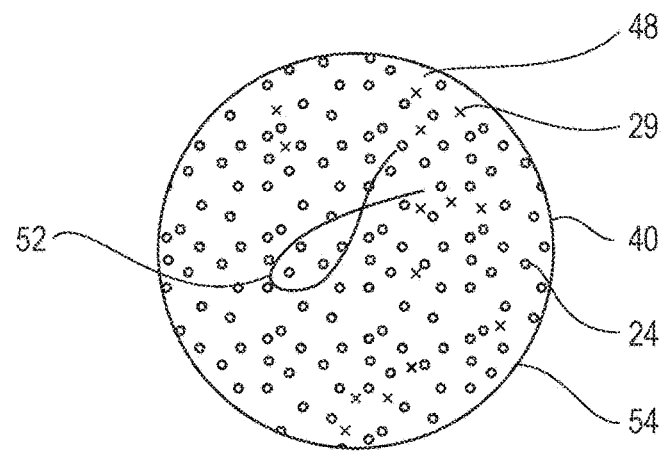
FIG. 13 is a transverse cross section of the composite gel marker embodiment of FIG. 12 taken along lines 13-13 of FIG. 12.
Figure 14:
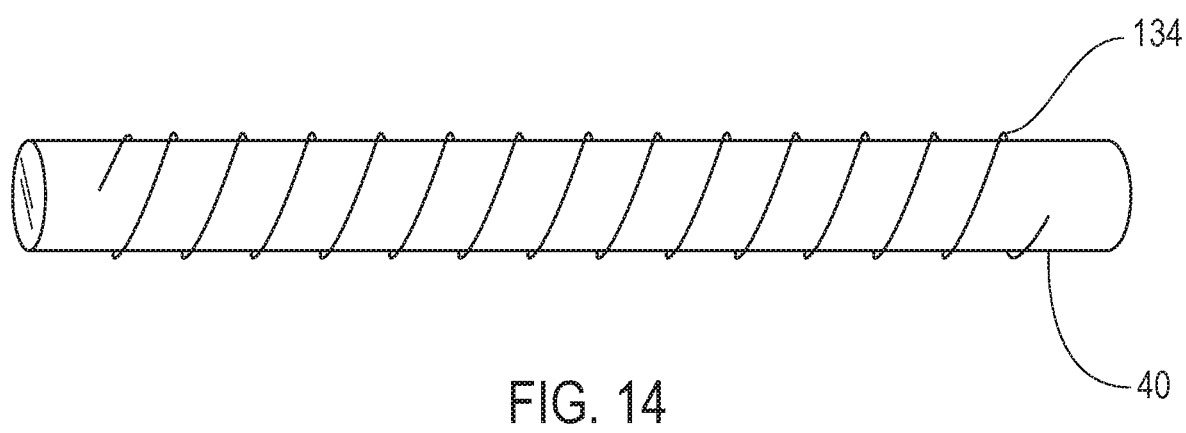
FIG. 14 is an elevation view of a composite gel marker embodiment that has been wrapped with a composite wire embodiment.

Notwithstanding the foregoing discussion of the use of free-standing silica shells 24 for imaging purposes within a patient's body 12, in order for the silica shell embodiments 24 to maintain a stable position and provide a desired functionality and longevity after deployment into tissue of interest in a patient, it may be desirable to encapsulate a desired number of the silica shell embodiments 24 into a composite gel marker 40. As discussed above, such a composite gel marker 40 may include a gel material 48, a desired concentration of silica shells 24 bound by the gel material 48, as well as any other components that may also be bound by the gel material 48. For example, radiopaque imaging materials 29 or separate radiopaque markers 52, as shown in FIGS. 12 and 13, may be included in the composite gel marker 40 in order to facilitate imaging under x-ray based imaging methods such as fluoroscopy, CT and the like. Examples of such radiopaque imaging materials 29 and markers 52 may include gold, platinum, tantalum, bismuth, barium and the like. In some cases, the use of barium sulfate is contemplated for radiopacity wherein low amounts of barium sulfate may be useful for imaging with CT, fluoroscopy and the like. In some instances, barium sulfate mixed with gelatin material 48 in a ratio of at least about 1 percent barium sulfate to gel material 48 by weight has been found to be imageable by mammography. For such embodiments, barium sulfate powder having a particle size of about 2 microns to about 5 microns may be useful. Imaging materials suitable for MRI use such as gadolinium including compounds such as gadolinium DTPA, ferrous gluconate, ferrous sulfate and the like may be included in the composite gel marker embodiments 40 in order to facilitate the MRI imaging modality.

Some embodiments of a multi-mode composite gel marker 40 for ultrasound imaging may include a plurality of silica shells 24, each silica shell 24 including a shell body 26 having a layer 28 which is formed from silica and a hollow void 34 disposed within the inner surface 35 of the silica layer 28 as shown in the silica shell embodiment 24 of FIG. 6. The composite gel marker 40 may also include an imaging material 29 which is configured to produce an imaging signal that is distinct from surrounding tissue and a hydroscopic gel material 48 which is disposed about the plurality of silica shells 24 and imaging material 29 so as to form an expandable composite gel marker body 54. For some embodiments of such a multi-mode composite gel marker 40, the plurality of silica shells 24 may include a shell body 26 having a first inner layer 28 which is formed from silica and a second layer 30 which is formed from silica, which is disposed on an outside surface 32 of the first inner layer 28, and which includes the imaging material 29 configured for producing an imaging signal which is distinct from surrounding tissue such as the silica shell embodiment 24 shown in FIG. 7. The silica shells 24 also include a hollow void 34 disposed within the inner surface 35 of the first inner layer 28. In some cases, a hydrophobic polymer coating 36 may be disposed on an outer surface 38 of the second layer 30 of the plurality of silica shells 24 as shown in FIG. 8.

Visually distinct imaging materials 29 including dyes such as methylene blue and the like may also be included in the gel material 48 of a composite gel marker 40 in order to make such a composite gel marker body 54 visually distinct from surrounding tissue once deployed to facilitate direct visual observation of such a gel marker embodiment 40. Any suitable or desirable combination of imaging materials 29 for imaging enhancement may be included in the shell structure of the silica shell embodiments 24 or in the gel material 48 of the composite gel marker embodiments 40 discussed herein that include such silica shells 24 in order to achieve the desired multi-mode imaging marker properties of various composite gel marker embodiments 40. For example, any of the imaging materials 29 such as radiopaque materials, MRI materials, visually distinct materials such as dyes may be included in either the structure of the silica shell embodiments 24 or encapsulated within or otherwise secured to the gel material 48 of composite gel marker embodiments 40 separately from the silica shell structures 24. Different types of silica shells 24 may also be included in particular composite gel marker embodiments 40. For example, some composite gel marker embodiments 40 may include silica shells 24 of varying diameter, wall thickness, coating thickness, imaging function and the like in order to provide a desired variation in longevity, function, time release function or any other desirable function. Furthermore, some composite gel marker embodiments 40 may include a variety of silica shells that have different imaging materials. For example, some embodiments of a single composite gel marker may include a plurality of silica shells 24 having a radiopaque imaging material 29 in the outer layer 30, additional silica shells having an MRI imaging material 29 in the outer layer 30, and still further additional silica shells 24 having a visually distinct imaging material 29, such as a dye like methylene blue, in the outer layer 30. As such, each type of silica shell 24 having a different imaging material 29 may serve a different imaging function within the same composite gel marker embodiment 40. Some embodiments of composite gel marker bodies 54 of such multi-mode composite gel markers 40 may include ratios of about 0.1 mg/ml to about 8.0 mg/ml of silica shell embodiments 24 to volume of gel material 48.

FIG. 12 shows a molding process whereby a plurality of silica shells 24 are being bound together and encapsulated by the gel material 48 with a single gamma shaped radiopaque ribbon marker 52 by a gel material 48 that is molded into an inner cylindrical cavity of a silicone tube 50. The resulting multi-mode composite gel marker 40 may then be pushed out of the inner cylindrical cavity and further processed by compressing the composite gel marker body 54 in order to reduce the volume and outer profile such that the composite gel marker 40 may then be loaded into a distal portion of an inner lumen of a cannula of an applicator, such as the applicator shown in FIGS. 16-24. The composite gel marker embodiment 40 may also be compressed and in some cases de-aired after being freeze dried while still disposed within an inner lumen of a silicone tube 50. In general, some such composite gel marker embodiments 40 may have an unexpanded dry length of about 2 mm to about 40 mm and an unexpanded dry transverse outer dimension of about 0.5 mm to about 2 mm. In some cases, such composite gel markers 40 may include gel materials 48 having properties specific to biocompatibility, duration or longevity in an in vivo implanted circumstance, expansion ratio when exposed to aqueous fluids, expansion rate when exposed to aqueous fluids and the like.

Figure 15:
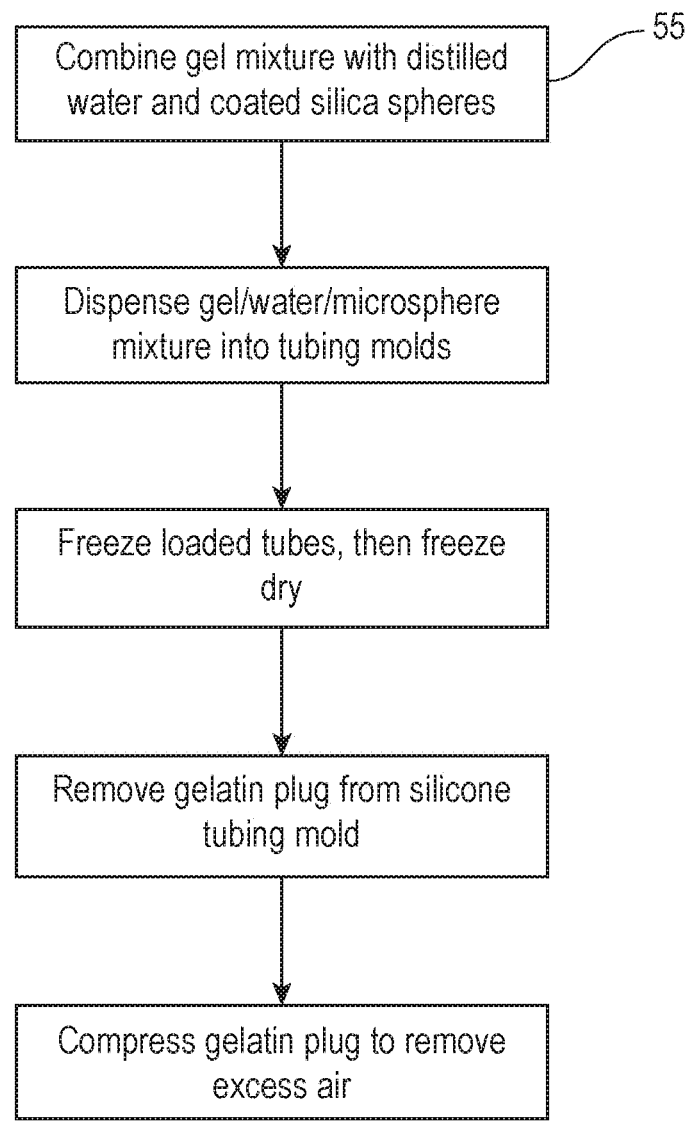
FIG. 15 is a flow chart of a molding method embodiment as shown in FIG. 12.
Figure 16:
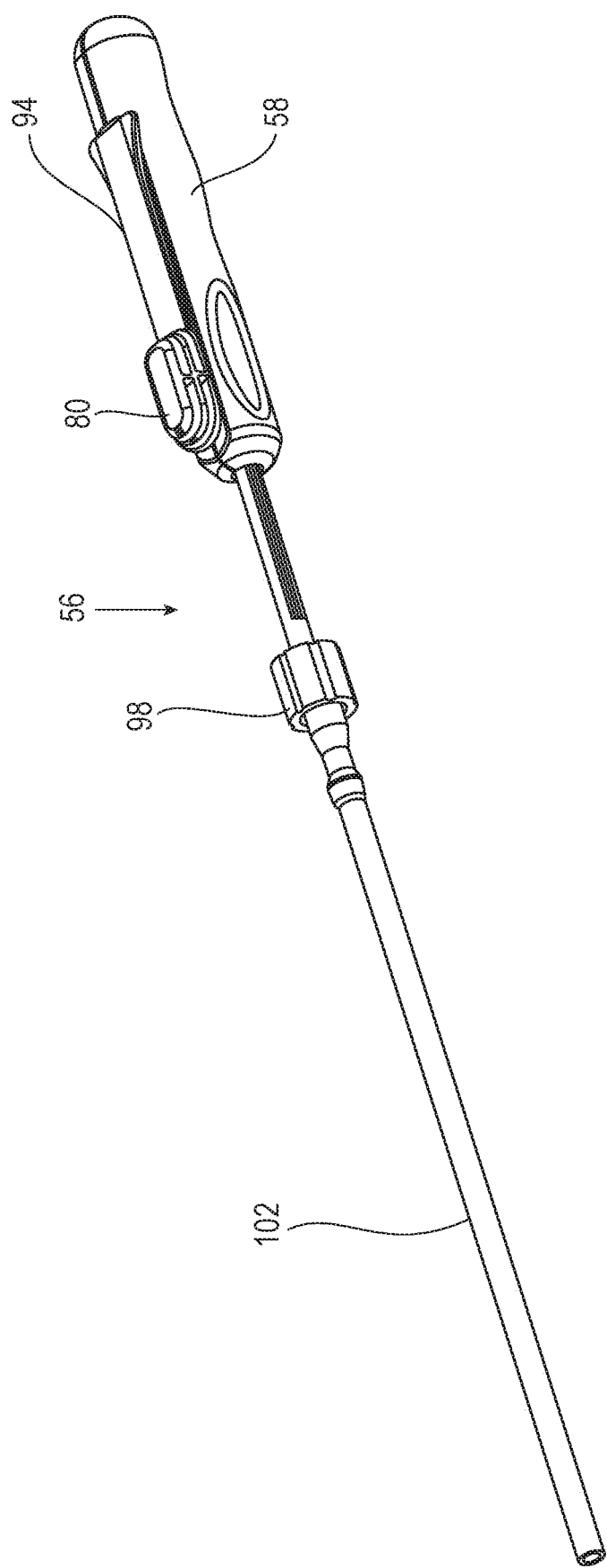
FIG. 16 is a perspective view of an applicator, also referred to as a marker deployment device, for deployment of composite gel marker embodiments as shown in FIGS. 12 and 13 with a cannula retraction knob and elongate cannula in a distal non-deployed position.
Figure 17:
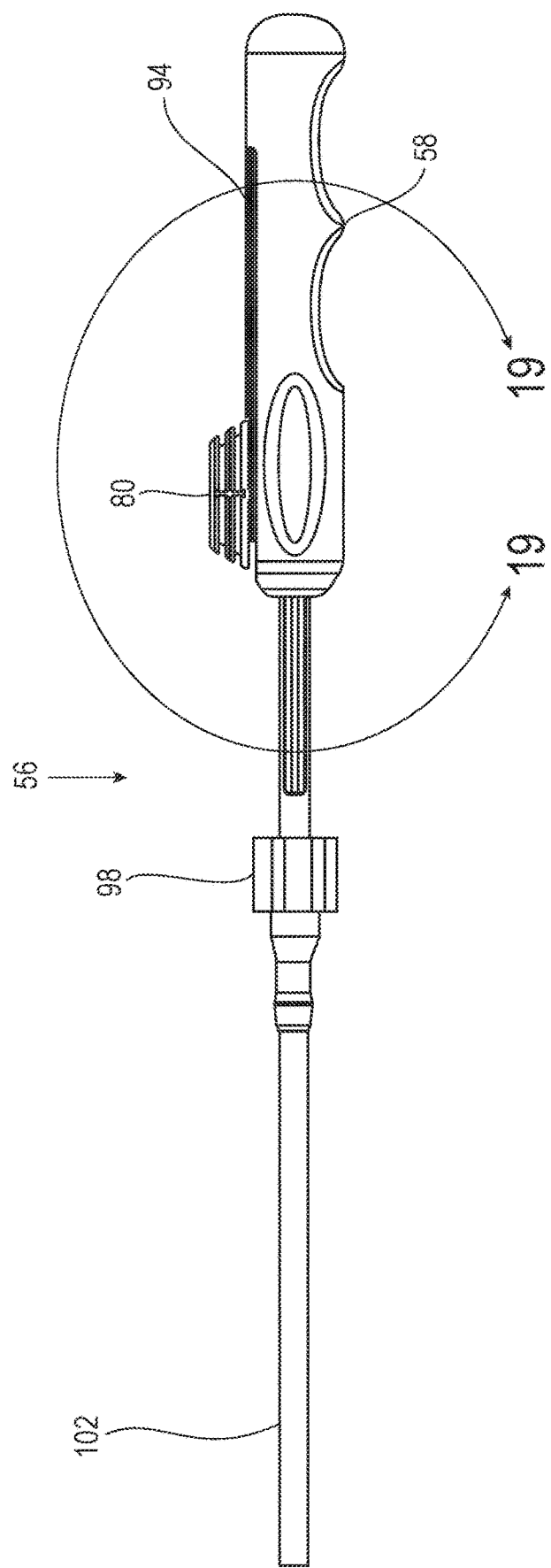
FIG. 17 is an elevation view of the applicator of FIG. 16.
Figure 18:
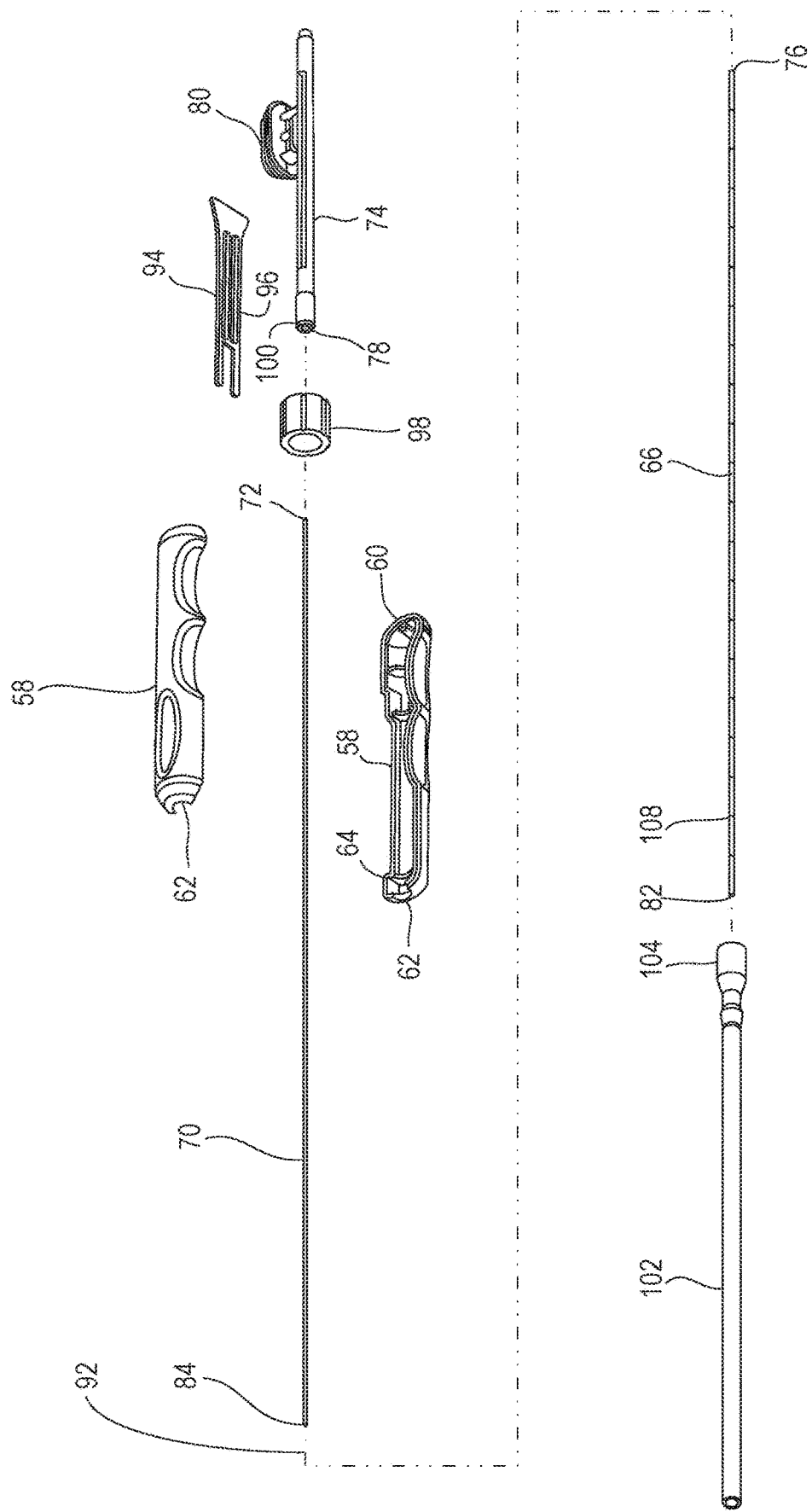
FIG. 18 is an exploded perspective view of the applicator of FIG. 16.
Figure 19:
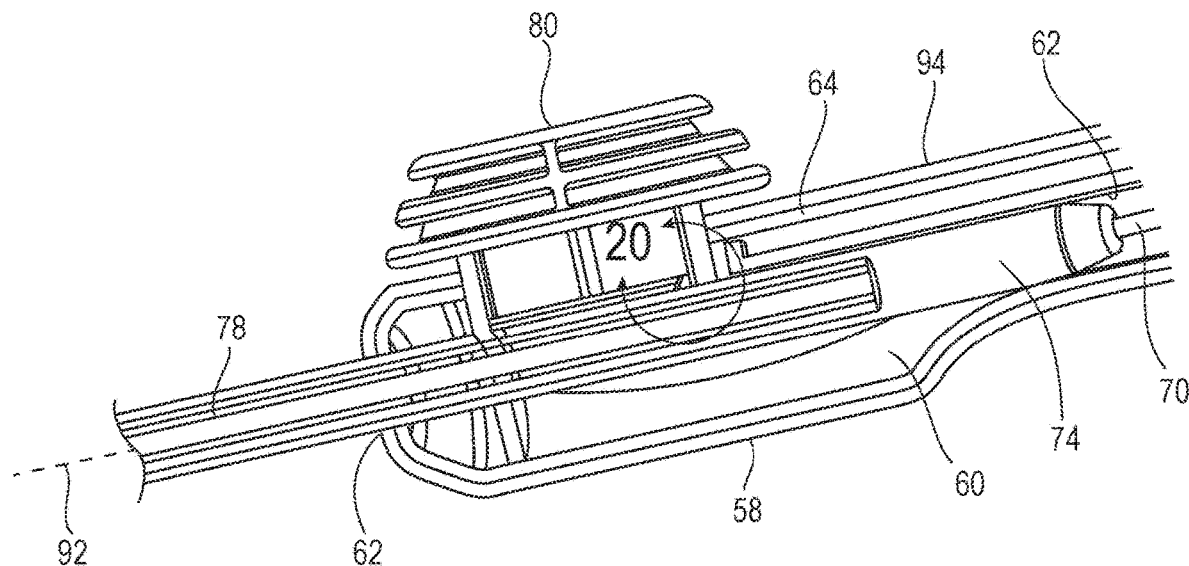
FIG. 19 is an enlarged view in section of the applicator of FIG. 17 taken along lines 19-19 of FIG. 17.

In some cases, multi-mode composite gel markers 40 may be constructed according generally to the process steps of the flowchart 55 shown in FIG. 15 wherein dry gel material 48 is combined with distilled water and any suitable silica shell embodiments 24 including any of those discussed herein. For some embodiments, the composition by weight of gel material 48, silica shells 24 and distilled water may be about 88% gel material 48, about 3% silica shells 24 and less than about 10% water. The gel-water-silica shell mixture may then be dispensed into an inner cylindrical cavity of a tubular mold made from a soft elastic material, such as the tubular silicone mold 50 shown in FIG. 12. A ribbon radiopaque marker embodiment 52 may also be included in the mixture dispensed into the cavity. The molded composite gel marker 40 may then be frozen and subsequently freeze dried.

Figure 24A:
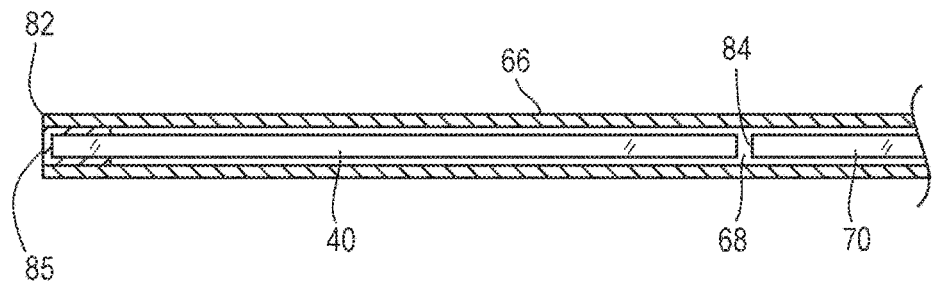
FIG. 24A is an enlarged view of encircled portion 24A-24A of the applicator of FIG. 23A showing the composite gel marker embodiment in a non-deployed position within the cannula.
Figure 24B:
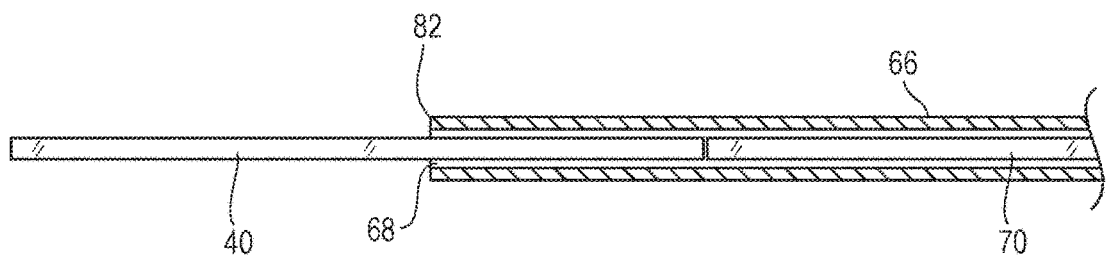
FIG. 24B is an enlarged view of encircled portion 24B-24B of the applicator of FIG. 23B showing the composite gel marker embodiment in a partially-deployed position disposed both within the cannula and outside the cannula.

Once freeze dried, the composite gel marker 40 may be pushed out of the cylindrical cavity of the silicone tubing 50 and compressed in order to remove air and reduce the transverse dimension and area so that the composite gel marker 40 will fit within the inner lumen of the distal portion of the cannula of the applicator as shown in FIG. 24A. For some embodiments, the freeze dried composite gel markers 40 may be compressed by rolling them between two silicone sheet surfaces (not shown) to remove air pockets and reduce profile. For some composite gel marker embodiments 40, gel materials 48, and particularly, hydrophilic gel materials 48 such as chitosan gel, porcine gel, collagen, methyl cellulose, polyethylene glycol (PEG), suitable polysaccharides, suitable hydrogels and the like may be used. It may also be desirable in some cases to adjust the formulation of the gel material 48 of the composite gel markers 40 in order to adjust the expansion time, duration of physical integrity of the composite gel marker 40 within the body 12 of a patient as well as other attributes. For some embodiments, the radiopaque ribbon marker 52 may be made from an elongate element of metallic radiopaque material such as gold, platinum, tantalum and the like.

In some cases, gelatin materials 48 may be manufactured using a variety of formulations in order to achieve desired properties of the finished material. For example, a gelatin material 48, such as Gelita Madella Pro 100, may be mixed with distilled water in a variety of ratios in order to tailor the resulting gelatin material properties to a particular indication or use. Such a gelatin material 48 may be mixed in ratios such as about 4 g of gelatin material to about 100 ml of distilled water, about 4.5 g gelatin material to about 100 ml of distilled water, or 5.0 g of gelatin material to about 100 ml of distilled water. Gelatin formulations mixed at these various ratios may then dispensed into an inner lumen of a silicone tube 50 having a length of about 3 cm and a transverse inner dimension of the inner lumen of about 2 mm, about 2.4 mm or any other suitable inner transverse dimension. After injection into the inner lumen, the gelatin formulations 48 and silicone tubing 50 disposed about the gelatin material 48 may then be frozen. Thereafter, the gelatin material 48 disposed inside the silicone tubing 50 may be freeze dried. After freeze drying, the gelatin material 48 may be rolled under pressure so as to remove air from the gelatin material 48 and reduce the overall volume of the gelatin material 48.

For gelatin materials 48 subjected to these processes, an outer transverse dimension of gelatin molded in 2 mm silicone tubes may be about 0.025 inches to about 0.031 inches, more specifically, about 0.026 inches to about 0.030 inches, and even more specifically, about 0.027 inches to about 0.028 inches. These rolled gelatin pads may also have a dry weight of about 7 mg to about 7.8 mg and in some cases, an axial length of about 22 mm to about 24 mm. Upon soaking such gelatin pads in water, the gelatin pads may expand to an outer transverse dimension of about 1.5 mm with an axial length of about 23 mm to about 25 mm in some cases. For gelatin materials subjected to these processes, an outer transverse dimension of gelatin molded in 2.4 mm silicone tubes may be about 0.026 inches to about 0.034 inches, more specifically, about 0.029 inches to about 0.033 inches, and even more specifically, about 0.031 inches to about 0.032 inches after being freeze dried and subsequently compressed. These rolled gelatin pads may have a dry weight of about 6.2 mg to about 8 mg.

Some embodiments of an applicator 56 for delivering a multi-mode composite gel marker 40 to a target site such as a tumor location, lesion location, area of interest location or the like within subdermal tissue of a patient 12 may include a handle 58 having an interior cavity 60, a slide bore 62 and a retraction slot 64. The applicator 56 may also include a cannula 66 having an inner lumen 68 extending a length thereof and a positioning rod 70 which is disposed within the inner lumen 68 of the cannula 66 and which has a proximal end 72 secured to the handle 58. The applicator embodiment 56 may also have a retraction shuttle 74 which is secured to a proximal end 76 of the cannula 66, which includes an inner lumen 78 that is coaxial with the inner lumen 68 of the cannula 66 and which slides within the slide bore 62 of the handle 58 thereby imparting relative axial displacement between the cannula 66 and the positioning rod 70. The applicator 56 may also include a retraction knob 80 which is secured to the retraction shuttle 74 and which is disposed within the retraction slot 64 of the handle 58 in a distal axial position such that the retraction slot 64 mechanically limits the axial movement of the retraction knob 80 and cannula 66 between the distal axial position (shown in FIGS. 16 and 23A) with a distal end 82 of the cannula 66 extending distally beyond a distal end 84 of the positioning rod 70 and a proximal axial position (shown in FIG. 23C) with the distal end 82 of the cannula 66 being disposed proximal of the distal end 84 of the positioning rod 70.

A composite gel marker 40 in an unexpanded state may be disposed in a cavity formed within the inner lumen 68 of the cannula 66 between the distal end 82 of the cannula 66 and the distal end 84 of the positioning rod 70 with the retraction knob 80 and cannula 66 in the distal axial position. The composite gel marker 40 so disposed may include any of the composite gel marker embodiments 40 discussed herein. In some cases, it may be desirable to include an optional plug 85 within the inner lumen 68 of the cannula 66 that detachably secures the composite gel marker 40 to the inner lumen 68 of the cannula 66 in order to prevent the composite gel marker 40 disposed within the inner lumen 68 from accidentally falling out of the inner lumen 68 prior to deployment. An example of such a plug 85 is shown in FIG. 24A. Plug embodiments 85 may be formed as part of the composite gel marker body 54 (such as at a first or distal end 120 thereof discussed below) or may be formed separately between an inner surface of the inner lumen 68 of the cannula 66 and an outer surface of the composite gel marker 40. For some embodiments, plug 85 may be made from a gel material 48 such as PEG or the like. The plug 85 may be configured to break away and release the composite gel marker 40 upon actuation of the retraction knob 80 as the distal end 82 of the cannula 66 is proximally retracted relative to the composite gel marker 40 and positioning rod 70.

Figure 20:
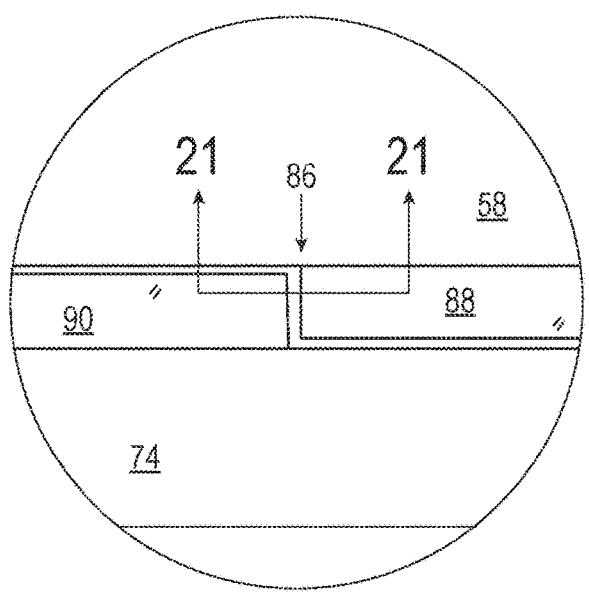
FIG. 20 is an enlarged view of the encircled portion 20-20 of the applicator shown in FIG. 19.
Figure 21:
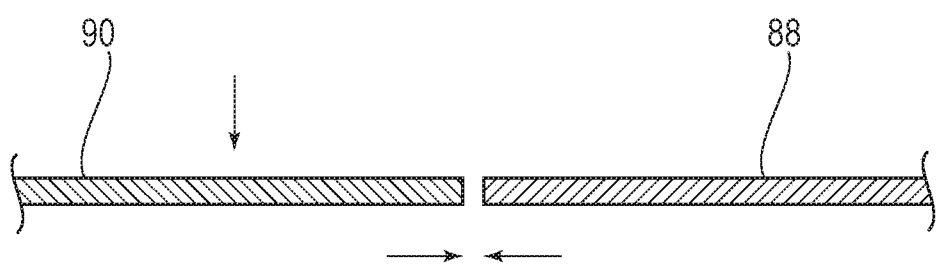
FIG. 21 is an elevation view of an interlock formed between a fin of the shuttle and a webbing of the housing of the applicator in a locked position.
Figure 22:
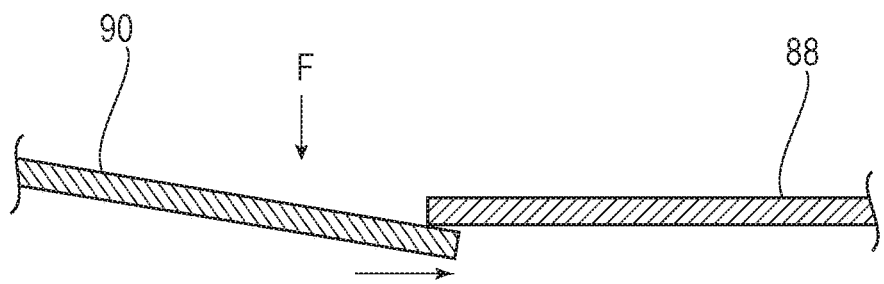
FIG. 22 shows the interlock of FIG. 21 in an unlocked position.

In some instances, the applicator 56 may also include an interlock 86 which has a first tab 88 secured to and extending inwardly from an inner surface of the interior cavity 60 of the handle 58 and a second tab 90 extending outwardly from the retraction shuttle 74. The second tab 90 may be in an overlapped configuration with respect to the first tab 88 along a direction substantially parallel to a longitudinal axis 92 of the positioning rod 70 and cannula 66 such that proximal retraction of the retraction knob 74 while in the distal axial position is mechanically prevented by the overlapped configuration of the first tab 88 and second tab 90 (as shown in FIGS. 20 and 21) until the retraction knob 80 is depressed by a downward force F so as to eliminate the overlap between the first tab 88 and second tab 90 (as shown in FIG. 22). For some embodiments, such applicators 56 may also have a removable interlock 94 including a removable block 96 having a snap fit into the retraction slot 64 proximal of the retraction knob 80 when the retraction knob 80 is in the distal axial position. This configuration serves to mechanically prevent proximal retraction of the retraction knob 80 until the removable interlock 94 is manually removed from the retraction slot 64. A Luer fitting 98 having an inner lumen is disposed on and secured to a distal end 100 of the retraction shuttle 74 with the inner lumen of the Luer fitting 98 being in fluid communication and coaxial with the inner lumen 68 of the cannula 66. A shield 102 which is removable and which has a rigid tubular body is disposed over the cannula 66 and is secured to the Luer fitting 98 of the retraction shuttle 74 with a corresponding Luer fitting 104 secured to a proximal end of the rigid tubular body of the shield 102. The shield 102 is used to protect the cannula 66 during storage and shipment of the applicator 56 prior to use.

Figure 28:
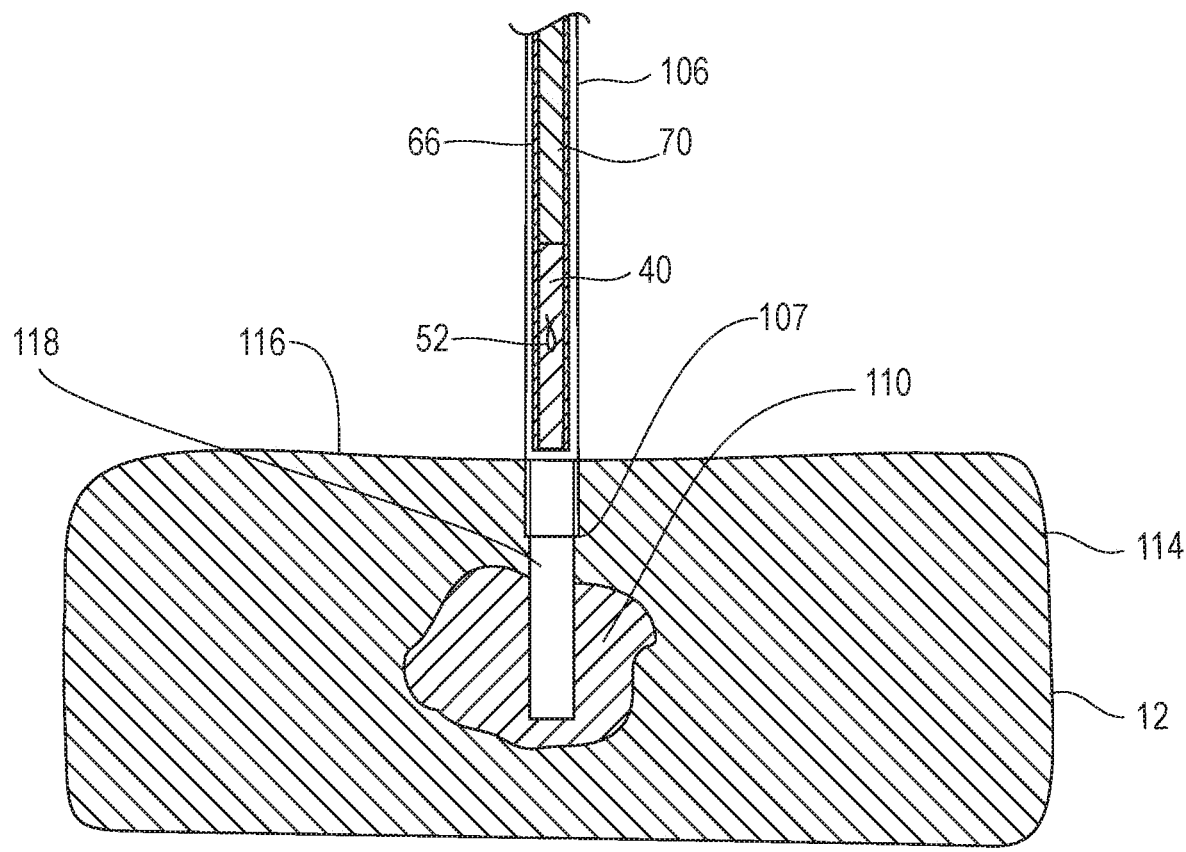
FIG. 28 shows a distal end of the cannula of the applicator of FIG. 16 disposed above the void left in the lung tissue from the previous biopsy process.
Figure 29:
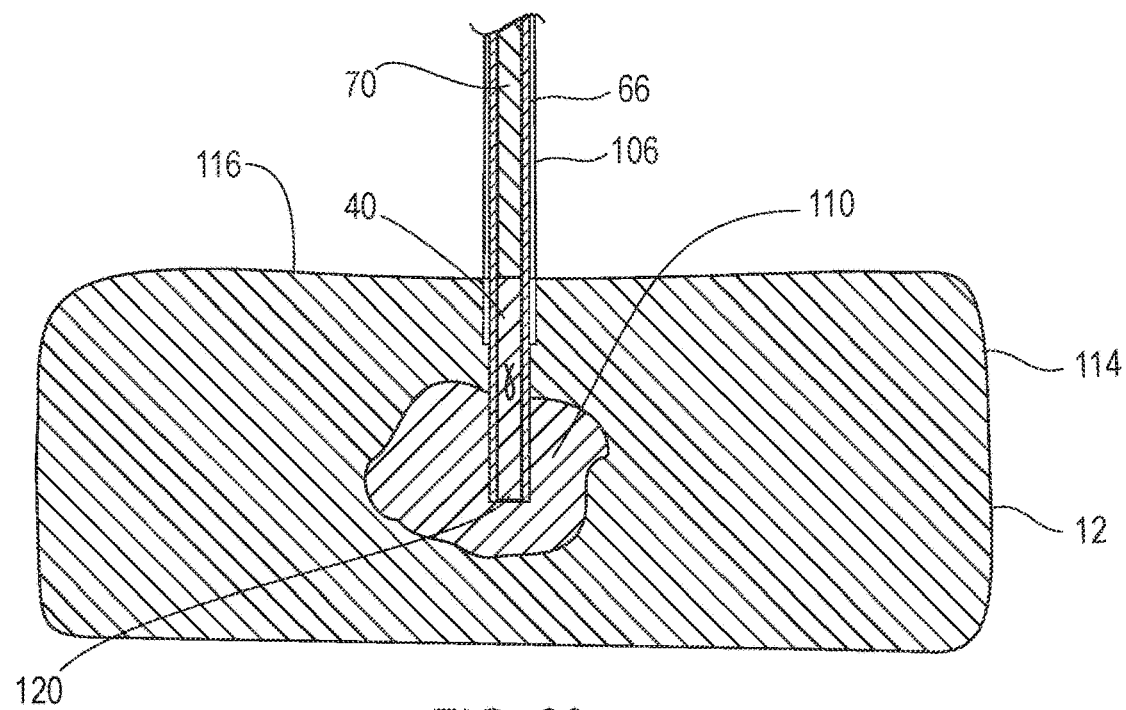
FIG. 29 shows a distal portion of the cannula of a loaded applicator disposed within the void left by removal of the biopsy sample with a first end of the composite gel marker embodiment disposed within the void within the tumor and a second end of the composite gel marker disposed adjacent an outer surface of the lung.
Figure 30:
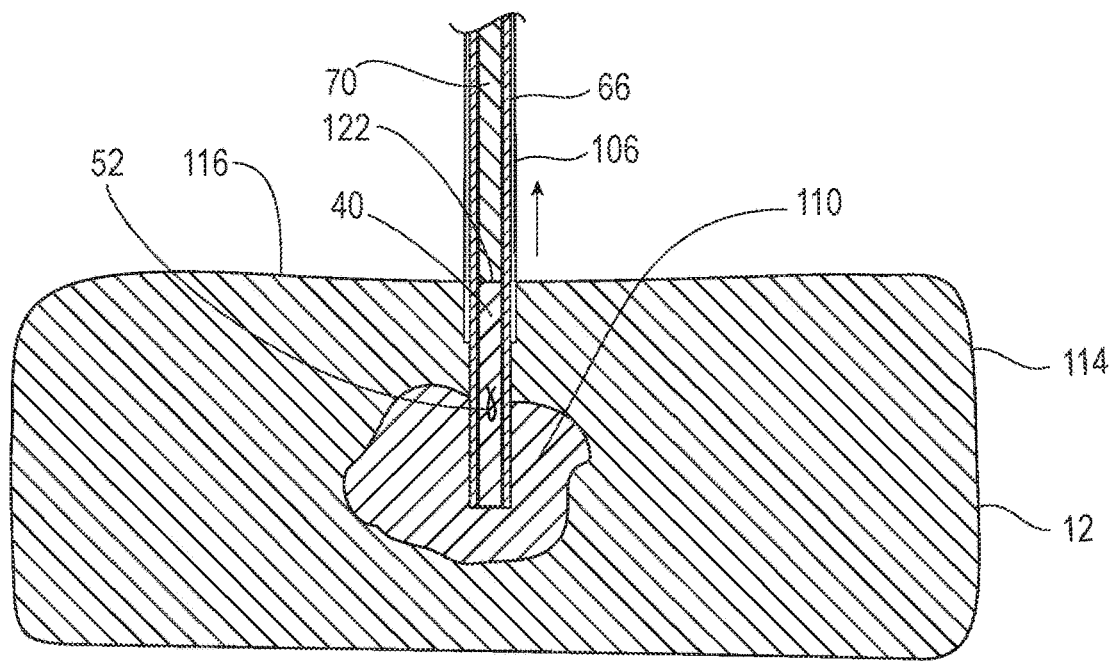
FIG. 30 shows proximal retraction of the cannula of the applicator while a positioning rod of the applicator presses against the second end of the composite gel marker to maintain the axial position of the composite marker relative to the surrounding tissue during the retraction of the cannula.

Some applicator embodiments 56 for use in deploying composite gel markers 40 including such freeze dried gel pads may be configured to fit smoothly into an inner lumen of currently available 19 gauge introducer devices 106 (as shown in FIGS. 28-30), include a luer lock fitting 98 that is compatible with currently available 19 gauge introducer devices 106, and include 0.5 cm spaced depth insertion markings 108 on a shaft thereof. It may also be useful for such applicator embodiments 56 to have a smooth and low force actuation/deployment mechanism, to be light weight and suitable for single-handed deployment of composite gel markers 40, and include a mechanism for preventing inadvertent deployment of composite gel markers therefrom, such as the interlock 86 and removable interlock 94, discussed above. Such an applicator 56 for the deployment of composite gel marker may be suitable for marking tumors within tissue of a patient's body 12 within 1 cm of a target location and mark lung tumors within 3 cm of the tumor location.

Figure 23A:
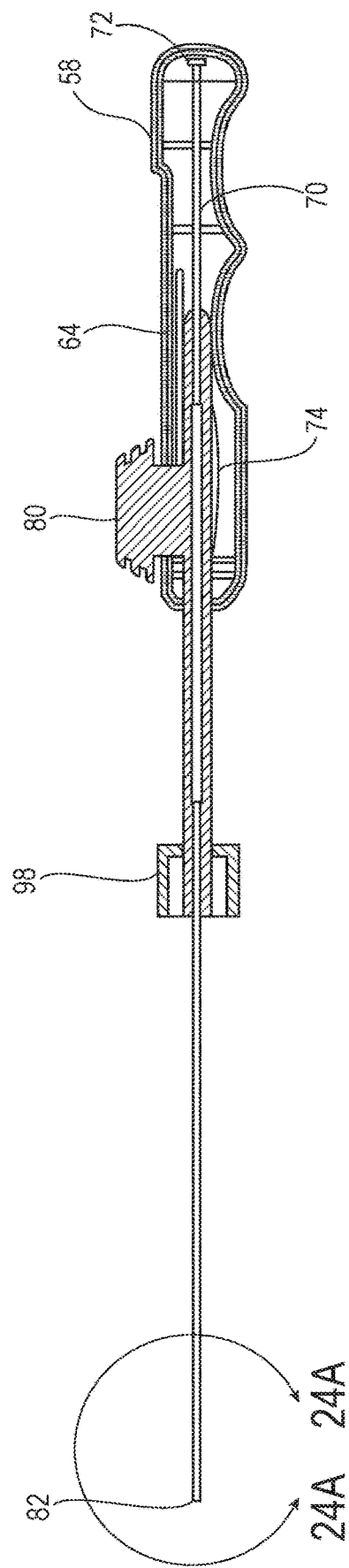
FIG. 23A is an elevation view in longitudinal section of the applicator of FIG. 16 with the retraction knob and cannula in a distal non-deployed position.
Figure 23B:
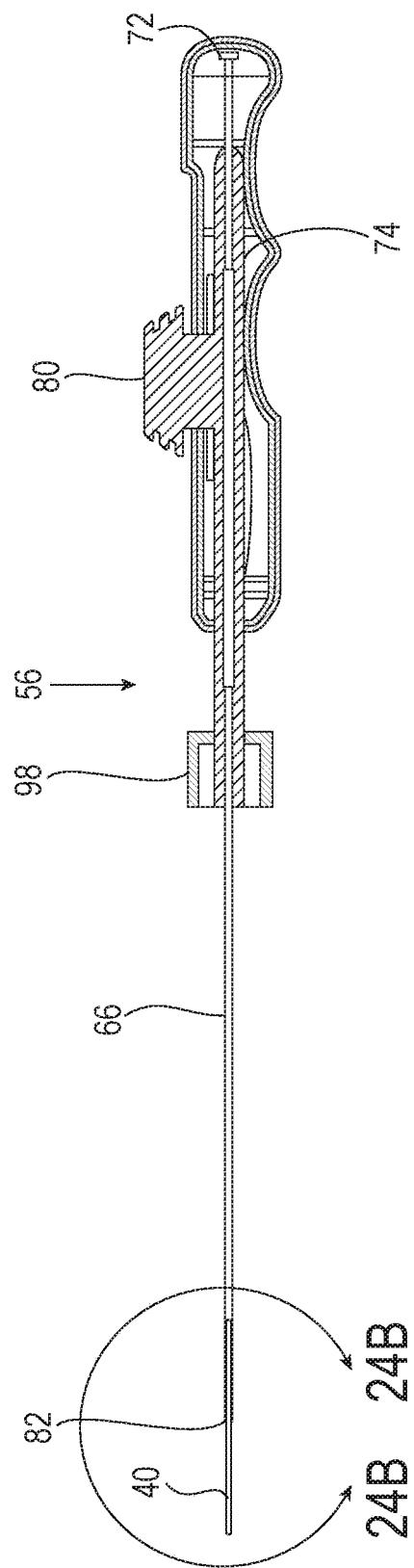
FIG. 23B is an elevation view in longitudinal section of the applicator of FIG. 16 with the retraction knob and cannula in an intermediate partially-deployed position.
Figure 23C:
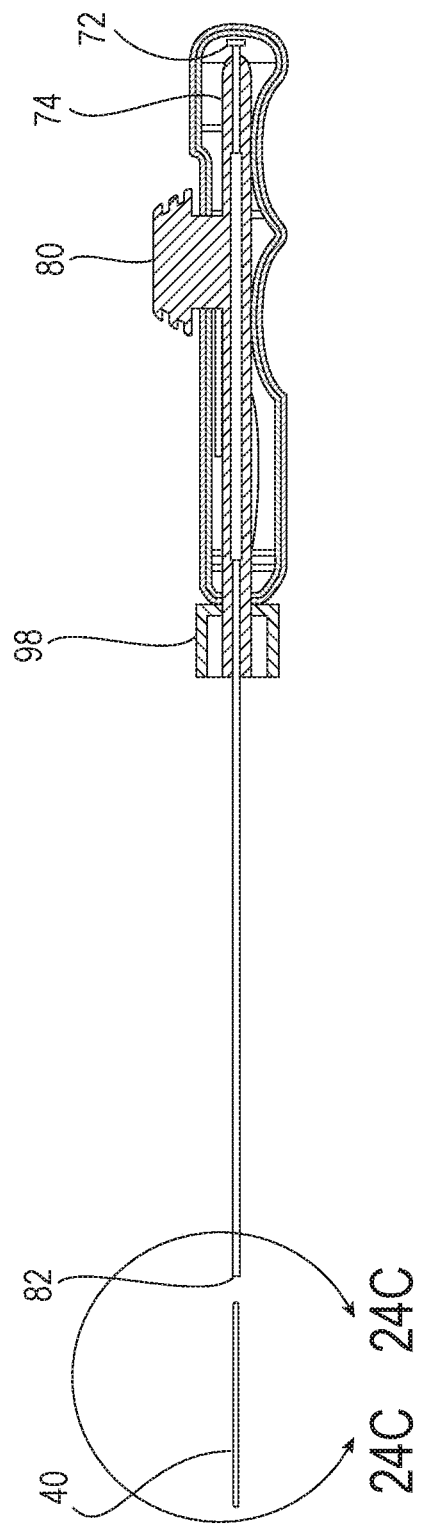
FIG. 23C is an elevation view in longitudinal section of the applicator of FIG. 16 with the retraction knob and cannula in a proximal deployed position.
Figure 24C:
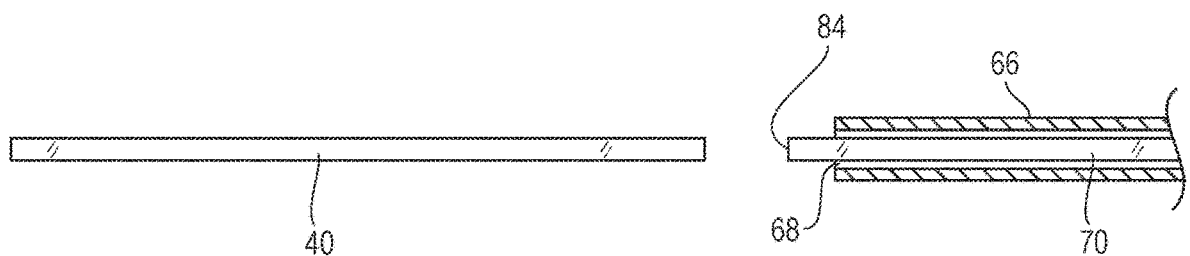
FIG. 24C is an enlarged view of encircled portion 24C-24C of the applicator of FIG. 23C showing the composite gel marker embodiment in a deployed position outside and distal of the cannula.
Figure 25:
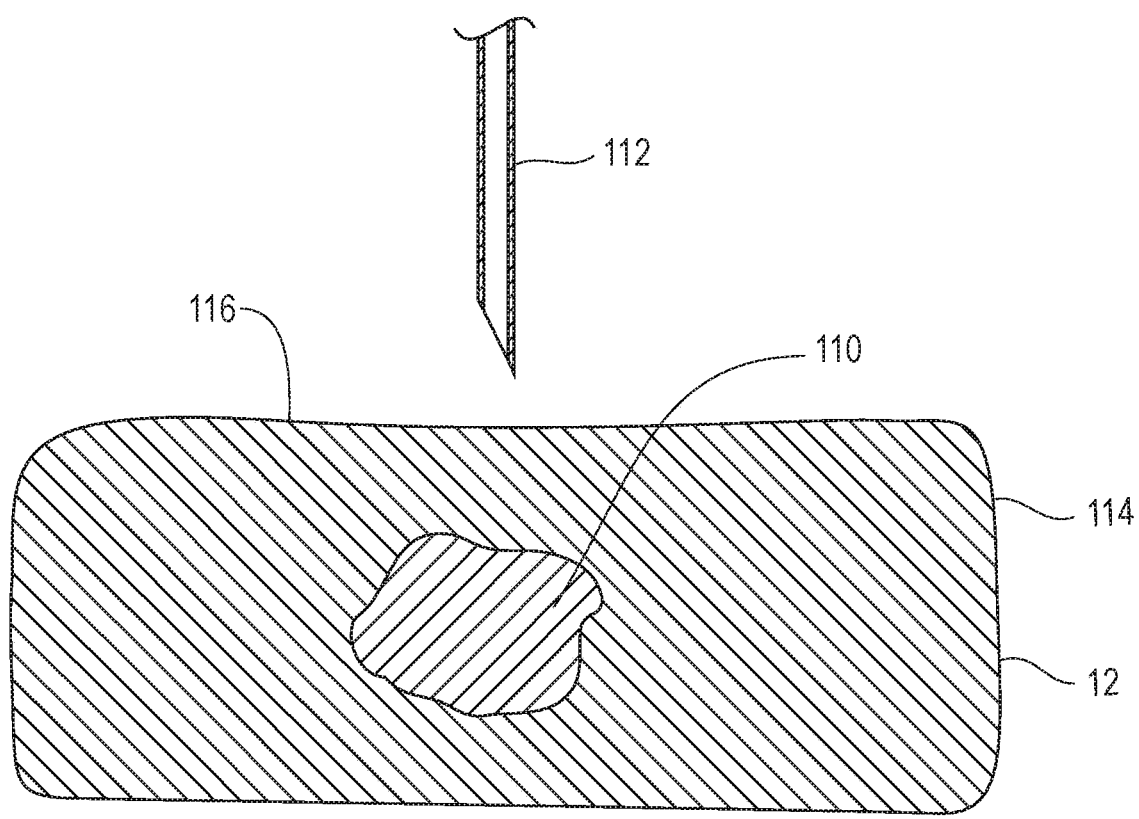
FIG. 25 is an elevation view in partial section and partially broken away showing a distal end of a biopsy cannula disposed above lung tissue of a patient and a tumor disposed below a surface of the lung tissue.

As discussed above, FIGS. 16-24C illustrate an embodiment of an applicator 56 that may be used to deploy one or more markers such as the composite gel marker embodiments 40 shown in FIGS. 12 and 13. As discussed above, some applicator embodiments 56 include a handle 58, a cannula 66 that is configured to advance into tissue, and a positioning rod 70 that is disposed in fixed relation with the handle 58. A retraction knob 80 is slidingly disposed relative to the handle 58 in an axial direction and is secured to the retraction shuttle 74 which is in turn secured to a proximal end 76 of the cannula 66 such that the retraction knob 80 and proximal end 76 of the cannula 66 may be axially displaced over a limited range of axial motion defined by the retraction slot 64 in the handle 58 in which the retraction knob 80 is captured. For such an arrangement, with the retraction knob 80 and cannula 66 slid distally forward relative to the positioning rod 70, there is an axial gap in the inner lumen 68 of the cannula 66 between the distal end 84 of the positioning rod 70 and distal end 82 of the cannula 66 that has a length and transverse dimension sufficient to accommodate an outer dimension of composite gel marker embodiments 40 disposed therein. When the retraction knob 80 and cannula 66 are proximally retracted relative to the handle 58 and positioning rod 70, one or more of the composite gel markers 40 may be exposed and deployed in place as the cannula 66 and positioning rod 70 are proximally withdrawn from the marker deployment target site 110 as shown in FIG. 25 for example. For this mode of deployment, it may be desirable for the retraction displacement of the retraction knob 80 and cannula 66 to be at least as great as an axial length of the composite gel marker 40 being deployed. For some embodiments, the retraction slot 64 and corresponding retraction displacement length may be about 1 cm to about 5 cm, more specifically, about 2 cm to about 4 cm. In addition, the applicator 56 may be configured to hold two or more composite gel makers 40 and deploy them sequentially with each retraction of the retraction knob 80. For the applicator embodiments 56 discussed above, the cannula 66 and positioning rod 70 may be from suitably resilient and high strength materials such as stainless steel. The handle 58, retraction shuttle 74, retraction knob 80, Luer fitting 98 as well as other components of these assemblies may be made from a suitable substantially rigid polymer such as ABS plastic, PVC plastic, or the like. For some embodiments, the cannula 66 may have a length of about 5 cm to about 20 cm and the corresponding positioning rod 70 sized to extend slightly beyond a distal end of the cannula 66 when the cannula is in a proximally retracted position as shown in FIGS. 23C and 24C. For some embodiments, the inner lumen 68 of the cannula 66 may have an inner diameter of about 0.5 mm to about 2 mm.

Figure 22A:
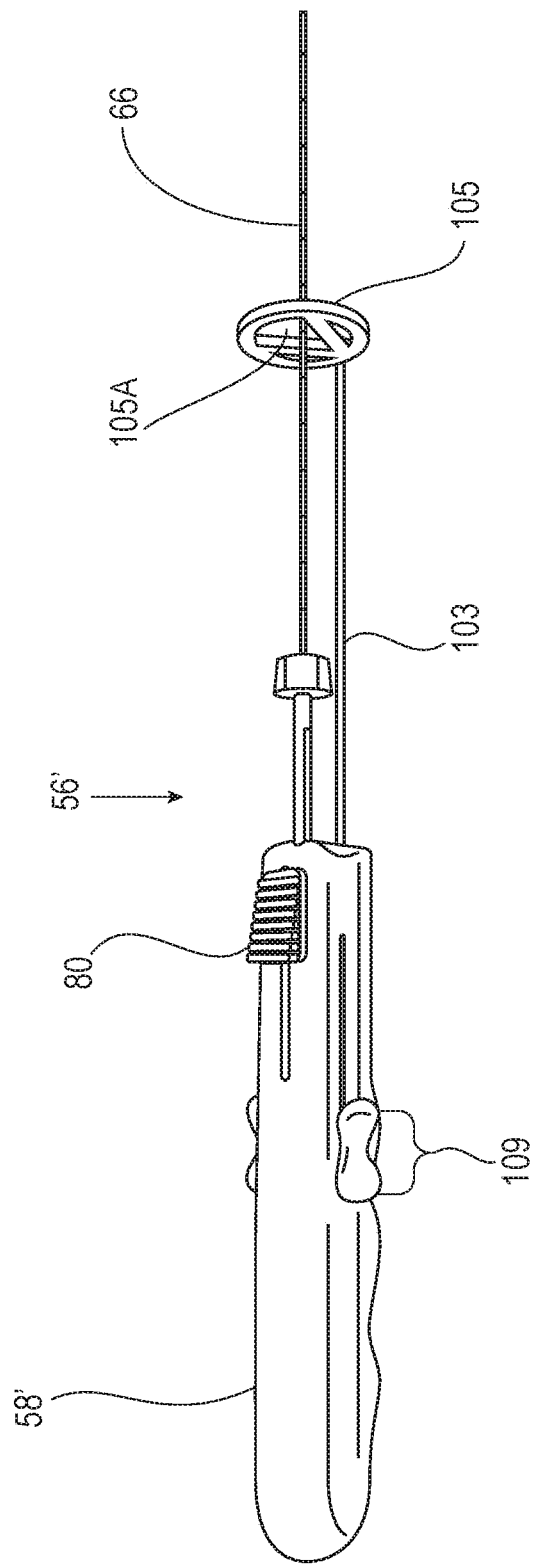
FIG. 22A is a perspective view of an applicator embodiment that includes an adjustable standoff.

FIG. 22A illustrates an embodiment of an applicator 56' that may have all of the same features, dimensions and materials as those of applicator 56 discussed above, but also includes and adjustable standoff 105 that is configured to adjustably limit a depth of penetration of the distal end 82 of the cannula 66 into the tissue of the patient 12 as measured from an outside surface level of the tissue. The standoff 105 has a substantially planar configuration that lies substantially perpendicular to the longitudinal axis 92 of the positioning rod 70. The standoff 105 further includes an aperture 105A through which the cannula 66 is slidingly disposed. The standoff 105 is supported by a rigid standoff shaft 103 that is secured to the standoff 105 at a distal end thereof and to a ratcheting shuttle 109 at a proximal end thereof. The ratcheting shuttle 109 is coupled to the handle 58' such that when radially depressed, the ratcheting shuttle 109 can be translated in an axial direction substantially parallel to the longitudinal axis 92 of the positioning rod 70 so as to correspondingly translate the standoff 105 in an axial direction relative to the cannula 66. The standoff 105 provides sufficient surface area against an outside surface of a patient's tissue such the handle 58' may be lightly pushed in the direction of the tissue surface in order to fix the position of the handle 58' relative to the position of the tissue surface. As such, the axial adjustment of the standoff 105 as carried out by ratcheting axial adjustment of the ratcheting shuttle 109 may be used to set a depth of penetration of the cannula 66 into a patient's tissue. In some cases, the ratcheting shuttle 109 may be configured to release the axial position of the ratcheting shuttle 109 by disengaging associated ratcheting surfaces of the respective ratcheting shuttle 109 and handle 58' when the ratcheting shuttle 109 is radially depressed against a resilient biasing force. The ratcheting shuttle 109 may then be temporarily locked in place with regard to axial position of the standoff 105 once the radially inward force is released and the associated ratcheting surfaces (not shown) re-engaged. In some cases, the standoff 105 may have an axial range of adjustment of about 2 cm to about 20 cm. For some embodiments, the standoff 105 and ratcheting shuttle 109 may be made from a rigid polymer such as ABS plastic, PVC plastic or the like. The standoff shaft 103 may be made from a suitable high strength resilient material such as stainless steel or the like.

As discussed above, certain imaging modalities are not well suited for imaging certain types of tissue. The imaging of lung tissue with ultrasound is an example. The tissue of the lung is too spongy and porous with a large percentage of air pockets to be efficiently imaged with ultrasound imaging equipment in general. However, a need has been shown for minimally-invasive, low-cost, and convenient methods of lung tissue and particularly lung nodule localization. An ultrasound-visible marker placed well ahead of surgery could alleviate many of the issues associated with existing wire localization techniques for imaging lung nodules and the like. However, as discussed above, it is traditionally difficult to image the lung due with ultrasound to the air within the parenchyma and airways. Notwithstanding this difficulty, some silica shell embodiments 24 and associated composite gel marker embodiments 40 discussed herein may be used in lung parenchyma to image pulmonary tissue using ultrasound imaging.

Certain composite gel marker embodiments 40 that are generally hydrophilic may be useful as imaging signal conduits for deployment in tissue that is not otherwise conducive to transmission of a particular imaging energy. Some multi-mode composite gel marker embodiments 40 may include a strong return signal by an imaging modality such as ultrasound imaging, including color flow Doppler ultrasound imaging and the ability to function as an ultrasound imaging signal conduit. For such applications, a composite gel marker embodiment 40 may be used to mark a lesion in lung tissue of a patient 12 and also provide an ultrasound imaging signal conduit to the extremities of the composite gel marker 40 and the lesion 110 disposed about or adjacent to the composite gel marker 40.

Some methods of marking and ultrasound imaging a target site 110 disposed within lung tissue of a patient's body may include deploying a composite gel marker 40 at a target site 110 within lung tissue of the patient with the composite gel marker 40 extending from the target site 110 to an outer surface level of the patient's lung. Thereafter, the target site 110 may be imaged with ultrasound from the outer surface level of the patient's lung through the composite gel marker, particularly through a composite gel marker saturated with aqueous fluids, and to the target site 110 with an ultrasound imaging signal that travels through the composite gel marker 40 from the outer surface level to the target site 110. Such composite gel markers 40 may require a greater length than similar composite gel markers 40 not being used as imaging signal conduits. Some such embodiments of multi-mode composite gel markers 40 may have an axial length of about 1 cm to about 10 cm, more specifically, about 3 cm to about 8 cm. In some instances, composite gel marker embodiments 40 may include gelatin and 2 µm microspheres with a diameter of about 1.6 mm and a length of about 15 mm.

Figure 26:
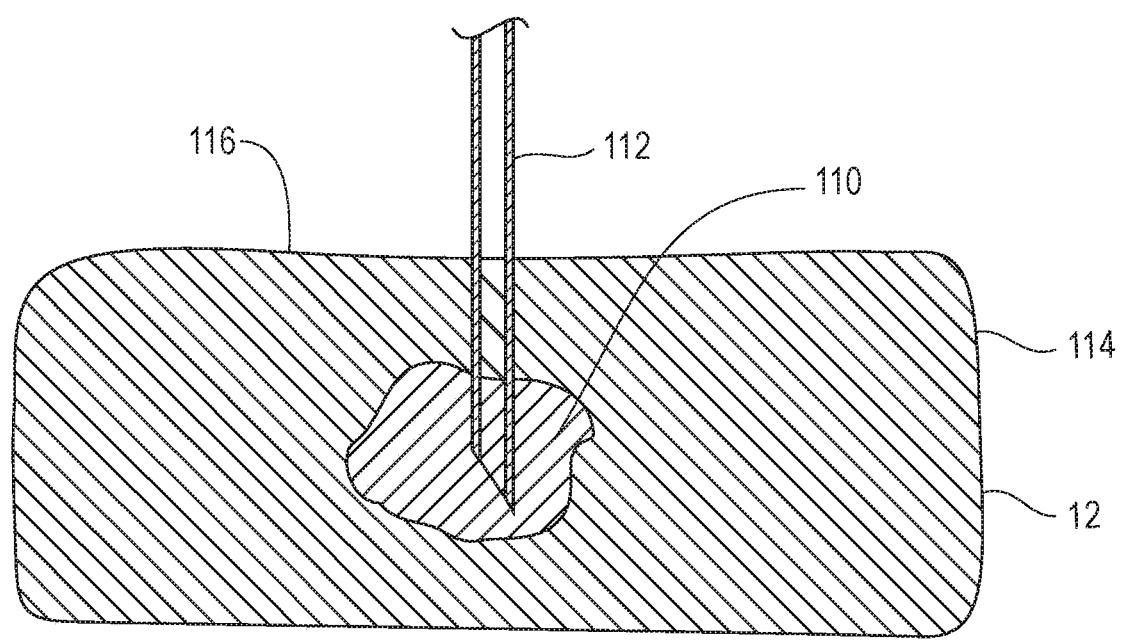
FIG. 26 shows the biopsy cannula advanced into the lung tissue of FIG. 25 with the distal end of the biopsy cannula disposed in the tumor.
Figure 27:
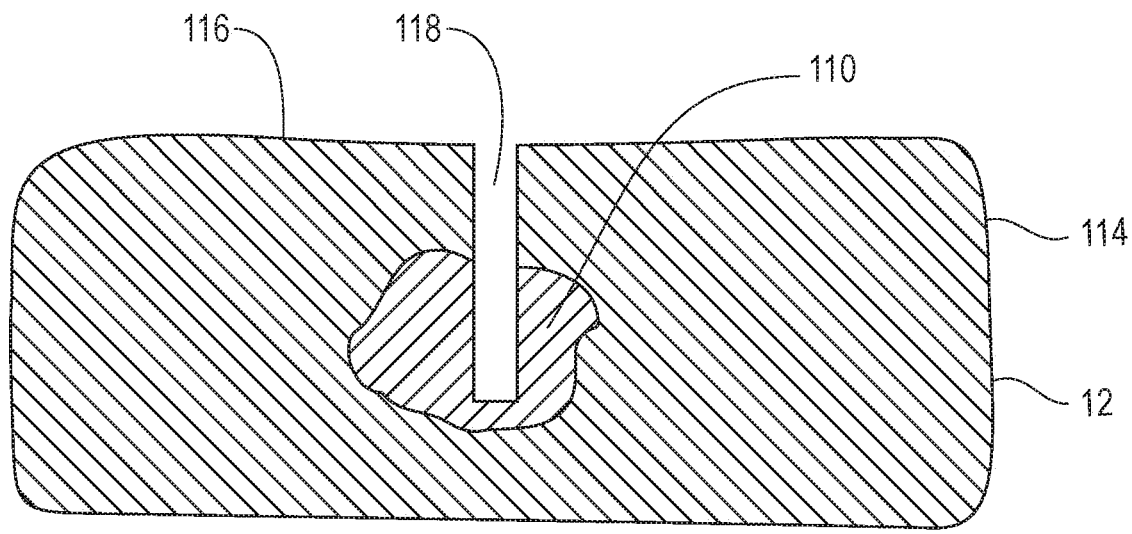
FIG. 27 shows the lung tissue of FIG. 26 after removal of a tissue sample from the tumor due to retraction of the biopsy cannula.

FIGS. 25-34 illustrate an embodiment of a medical procedure wherein a multi-mode composite gel marker embodiment 40 is being deployed in lung tissue 114. The composite gel marker 40 includes silica shells 24 as discussed above for color Doppler ultrasound imaging and visual identification due to the methylene blue component and a radiopaque ribbon 52 that is suitable for radiographic imaging such as fluoroscopy. The composite gel marker 40 may also include a radiopaque imaging material 29 such as a radiopaque powder that is dispersed throughout all or a portion of the composite gel marker body 54. In FIG. 25, a distal end of a biopsy cannula 112 is disposed above lung tissue 114 of a patient 12 and a tumor target site 110 is shown disposed below an outer surface 116 of the lung tissue 114. The biopsy cannula 112 is advanced into the lung tissue 114 as shown in FIG. 26 until the distal end of the biopsy cannula is disposed in the tumor 110. Once the biopsy cannula 112 has cut boundaries of the biopsy tissue to be sampled, the biopsy cannula 112 and biopsy sample may then be proximally retracted and removed from the patient's lung tissue 114. FIG. 27 shows the lung tissue 114 after removal of a tissue sample from the tumor 110 due to retraction of the biopsy cannula and with a channel 118 in the lung tissue 114 and tumor 110 where the biopsy sample was removed.

Figure 31:
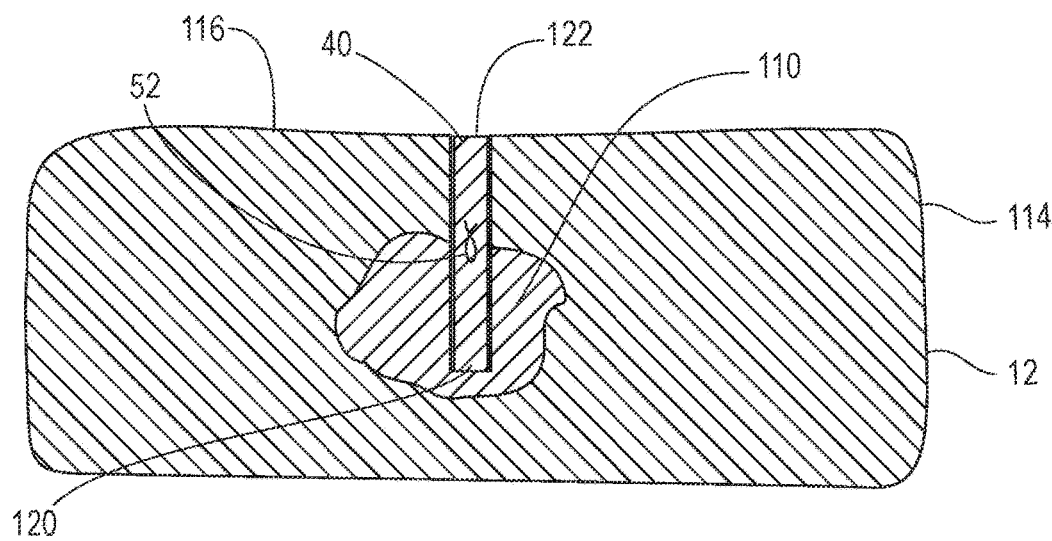
FIG. 31 shows the composite gel marker disposed within the tissue channel left by removal of the biopsy sample.

Thereafter, the cannula 66 of the applicator 56, the distal end 82 of which is loaded with a composite gel marker embodiment 40, may be distally advanced through an inner lumen of an optional introducer 106 and into the tissue channel 118 left in the lung tissue 114 from the previous biopsy process. The cannula 66 may be advanced until a first end 120 of the composite gel marker 40 is disposed within the channel 118 within the tumor 110 and a second end 122 of the composite gel marker 40 is disposed adjacent an outer surface 116 of the lung tissue 114 as shown in FIG. 29. The composite gel marker 40 may also be axially positioned such that the second end 122 of the composite gel marker 40 extends outwardly from the outer surface level 116 of the lung tissue 114 in some cases. For example, the second end 122 of the composite gel marker 40 may extend at least about 0.1 cm to about 1.0 cm from the surface 116 of the lung tissue 114 at the time of deployment in some instances. The cannula 66 of the applicator 56 may then be proximally retracted while the distal end 84 of the positioning rod 70 of the applicator 56 presses against the second end 122 of the composite gel marker 40 to maintain the axial position of the composite gel marker 40 relative to a position of the tissue of the target site 110 during the retraction of the cannula 66. For the applicator embodiment 56 shown in FIGS. 16-24C, the cannula 66 may be proximally withdrawn relative to the composite gel marker 40 by translating the retraction knob 80 in a proximal direction relative to the handle 58 and positioning rod 70 while maintaining the axial position of the handle 58 relative to the lung tissue 114. In addition, for the applicator embodiment 56 shown, prior to actuation of the retraction knob 80, the retraction knob 80 may first be depressed in an inward radial direction with force F relative to the longitudinal axis 92 of the positioning rod 70 in order to disengage the interlock 86 of the retraction shuttle 74 and handle 58 as shown in FIGS. 21 and 22. In addition, for some embodiments, the removable interlock 94 may be removed from the handle 58 such that the removable block 96 of the removable interlock 94 is disengaged from the retraction slot 64 of the handle 58 in order to enable proximal retraction of the retraction knob 80 by removing the mechanical interference of the removable interlock 94 with the retraction knob 80. Once the cannula 66 has been proximally retracted and the composite gel marker 40 deployed, the cannula 66 and positioning rod 70 of the applicator 56 may then be proximally withdrawn with the composite gel marker 40 disposed within the tissue channel 118 left by removal of the biopsy sample as shown in FIG. 31. The introducer 106 may also be proximally withdrawn from the tissue channel 118 at the same time or at any other suitable time during the procedure.

In some cases, if a biopsy is not performed prior to deployment of the composite gel marker 40, the introducer 106 may be advanced directly through the tissue 114, typically with a stylet (not shown) disposed within the inner lumen of the introducer 106. Such a stylet may extend just beyond a distal end of the introducer 106 and be configured so as to provide a pointed tissue penetrating tip for the introducer 106. Once the introducer is in place, the stylet may be proximally withdrawn from the inner lumen of the introducer 106. In some instances, for procedures utilizing an introducer 106, the introducer 106 may be positioned such that a distal end 107 of the introducer 106 is disposed about 1 cm to about 2 cm into the lung tissue 114 from the outer surface level 116. Other suitable positions for the distal end 107 of the introducer are also contemplated. It should also be noted that this procedure may be performed without the use of an introducer 106 or a pre-existing tissue channel 118. For some deployment embodiments, the cannula 66 of the applicator 56 may be advanced directly into lung tissue 114 to the target site under any suitable imaging modality such as fluoroscopy, CT, MRI or the like. Once the cannula 66 and the composite gel marker 40 disposed in a distal end 82 thereof are properly positioned at the target site 110, the composite gel marker 40 may then be deployed from the distal end 82 of the cannula 66 at the target site 110 as discussed above.

Figure 32:
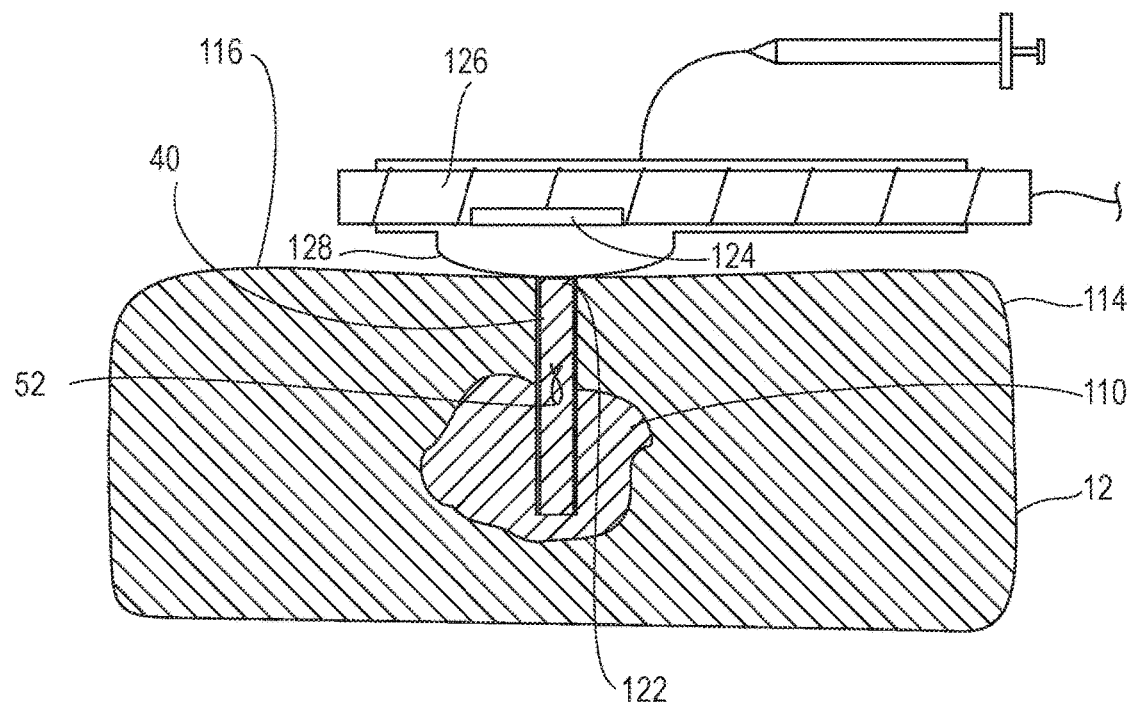
FIG. 32 shows the composite gel marker being imaged by an ultrasound system with a transducer window of a transducer disposed over the marker and with a liquid filled inflatable lens disposed between and in contact with the transducer window and the composite gel marker.

Once so deployed, the composite gel marker 40 may begin to expand and absorb surrounding aqueous body fluids due to a hydrophilic property of the gel material 48 in some cases as shown in FIG. 32. Such expansion may be useful in order to fill the void 118 left by the biopsied tissue and fix the position of the composite gel marker 40 relative to the surrounding lung tissue 114. The expanded composite gel marker 40 may also serve to seal the tissue channel 118 which may be useful to provide hemostasis at the biopsy site in some cases. It should be noted that the gel material 48 and processing may in some instances be chosen to adjust the expansion ratio and rate to desired values. In some cases, the composite gel marker 40 may have an expansion ratio by volume of about 1:1.5 to about 1:10, more specifically, about 1:2 to about 1:3.

The biopsy procedure embodiment and deployment procedure embodiment shown in FIGS. 25-32 may be carried out with the aid of one or more of any suitable type of imaging modality, including typically for this procedure visual imaging, fluoroscopic imaging, CT imaging, mammography, and MRI. For composite gel marker embodiments 40 that include MRI imaging materials 29, such materials may include gadolinium, ferrous gluconate, ferrous sulfate, titanium and the like. As discussed above, ultrasound imaging, including color Doppler ultrasound imaging, is not typically suitable for lung tissue indications due to the physiological properties of lung tissue 114. However, once the elongate composite gel marker 40 has been deployed with a second end 122 of the composite gel marker 40 disposed at or above the surface 116 of the lung tissue 114 and after the composite gel marker 40 has absorbed sufficient fluids, an ultrasound imaging signal may then propagate through the composite gel marker 40 down to the tumor 110 in the lung tissue 114. This imaging signal conduit of the composite gel marker 40 functions to aid the treating physician with imaging of the tumor with ultrasound imaging equipment 16 which may be a more suitable and convenient imaging modality as compared to other imaging modality options.

In some cases, lung injections for deploying composite gel marker embodiments 40 discussed herein may be performed using a 19-gauge introducer 106 with a 20-gauge needle. Such injections may be performed under CT or fluoroscopic guidance to confirm placement in the lung 114. Ultrasound imaging may be effectively performed on the composite gel marker embodiments 40 about 1 minute to about 10 minutes after injection in some cases. It has been shown that for some composite gel marker embodiments 40, ultrasound imaging may be performed using color Doppler through the thoracic wall to observe an implant site at about 1 minute to about 10 minutes after injection, 7 days after injection, 21 days after injection or at any other suitable time and still provide a highly visible ultrasound imaging signal. The area of composite gel marker placement may be imaged in some cases with Doppler ultrasound from the lung surface. Therefore, the composite gel marker embodiments 40 discussed herein may be placed during an initial pulmonary biopsy or at any point several weeks prior to planned surgical excision, facilitating scheduling on the day of surgery. Ultrasound imaging may then be used during thoracoscopic surgery or mini-thoracotomy to verify nodule location prior to resection.

Figure 33:
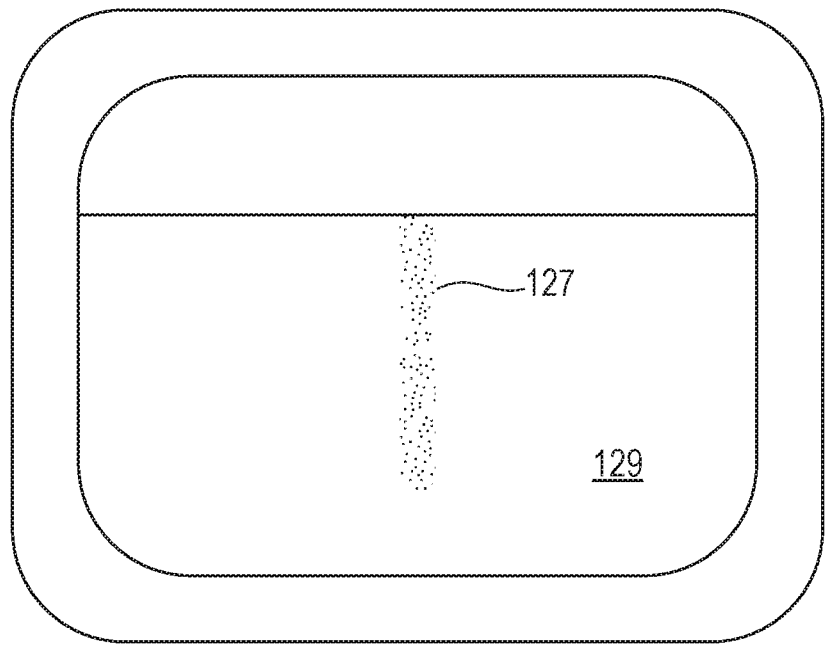
FIG. 33 shows a display screen depicting a visual image display embodiment of an ultrasound image of the expanded composite gel marker of FIG. 32.
Figure 34:
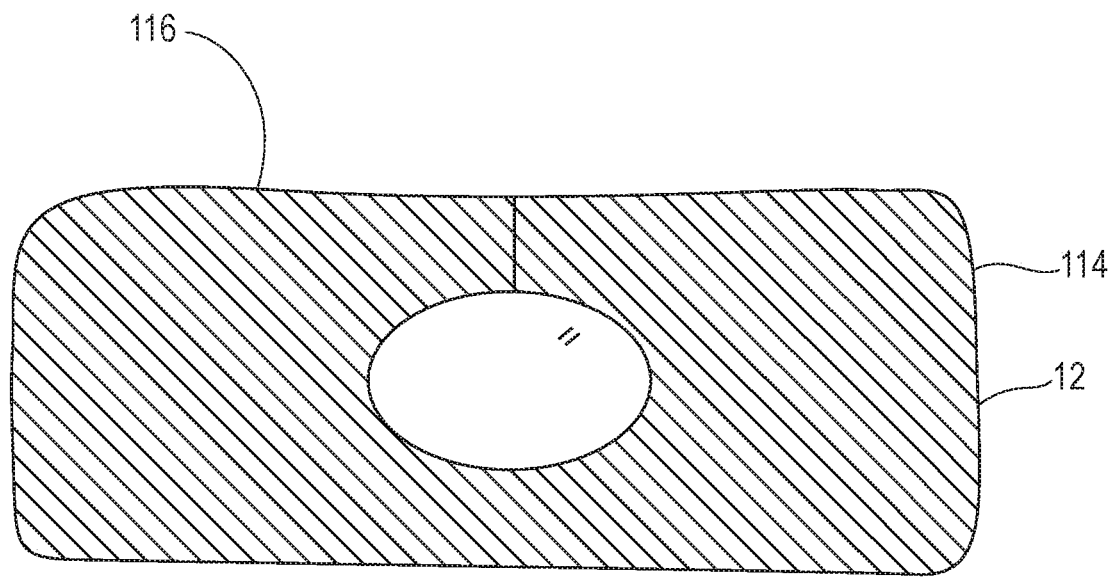
FIG. 34 shows the lung tissue of FIG. 32 with the tumor tissue and composite gel marker removed by surgical excision.

In addition, certain modifications or imaging options may be used in order to more efficiently image the lung tumor 110 using the imaging signal conduit formed by the expanded composite gel marker 40. For example, FIG. 32 shows the composite gel marker 40 and tumor 110 being imaged by an ultrasound system with a transducer window 124 of a transducer 126 disposed over the second end 122 of the composite gel marker 40 and with an optional liquid filled inflatable lens 128 disposed between and in contact with the transducer window 124 and the second end 122 of the composite gel marker 40. An example of a visual display of such imaging of the composite gel marker 40 and target site 110 is shown in FIG. 33 which shows the screen 129 of an ultrasound imaging system console during the imaging process. An imaged representation 127 of the composite gel marker embodiment 40 being imaged is shown on the display screen 129. Once the tumor 110 has been identified and located with ultrasound imaging, the tumor tissue 110 and composite gel marker 40 may be removed by surgical excision or any other suitable method as shown in FIG. 34. In some cases, the excision may be performed under ultrasound imaging guidance using the composite gel marker 40 as an imaging conduit up to such point that the composite gel marker 40 has also been removed from the lung tissue 114.

Some methods of marking and ultrasound imaging a target site within a patient's body may include preparing the applicator 56 for use by removing the shield 102 from the cannula 66 of the applicator 56 and advancing a distal end 82 of the cannula 66 of an applicator 56 to a target site 110 within a patient's body 12 below a surface of the patient's skin. In some cases, the target site 110 within the patient's body 12 may have been identified and located with an imaging modality other than an ultrasound imaging modality such as with fluoroscopy or MRI. In addition, in some instances, an introducer 106 may have been advanced to a target site 110 and the cannula 66 subsequently advanced through an inner lumen of the introducer 106 to the target site 110. In some cases, the position of the introducer 106 may be used to guide the axial position of the cannula 66 whereby the introducer 106 is placed in a position with a distal end thereof adjacent the target site 110. The cannula 66 may then be advanced through the inner lumen of the introducer 106 and secured relative to the introducer 106. For some embodiments, the cannula 66 may be secured relative to the introducer 106 by coupling respective Luer fittings of the cannula 66 and introducer 106.

The distal end 82 of the cannula 66 may be advanced such that a multi-mode composite gel marker 40 disposed within a cavity in an inner lumen 68 of the cannula 66 between a distal end 82 of the cannula 66 and a distal end 84 of a positioning rod 70 disposed within the inner lumen 68 of the cannula 66 is in a desired position relative to the target site 110. Such methods may also include proximally retracting the retraction knob 80 and the cannula 66 of the applicator 56 relative to tissue 114 of the target site 110, the composite gel marker 40, the positioning rod 70 and a handle 58 of the applicator 56 until the outer radial constraint of an inner surface of an inner lumen 68 of the cannula 66 is removed from the composite gel marker 40 so as to deploy the composite gel marker 40 at the target site 110. Thereafter, the cannula 66 and positioning rod 70 may be withdrawn from the patient's body 12. The composite gel marker 40 and adjacent target site 110 may subsequently be imaged with ultrasound imaging and the target site 110 optionally treated during or in conjunction with the ultrasound imaging of the target site 110.

Figure 35:
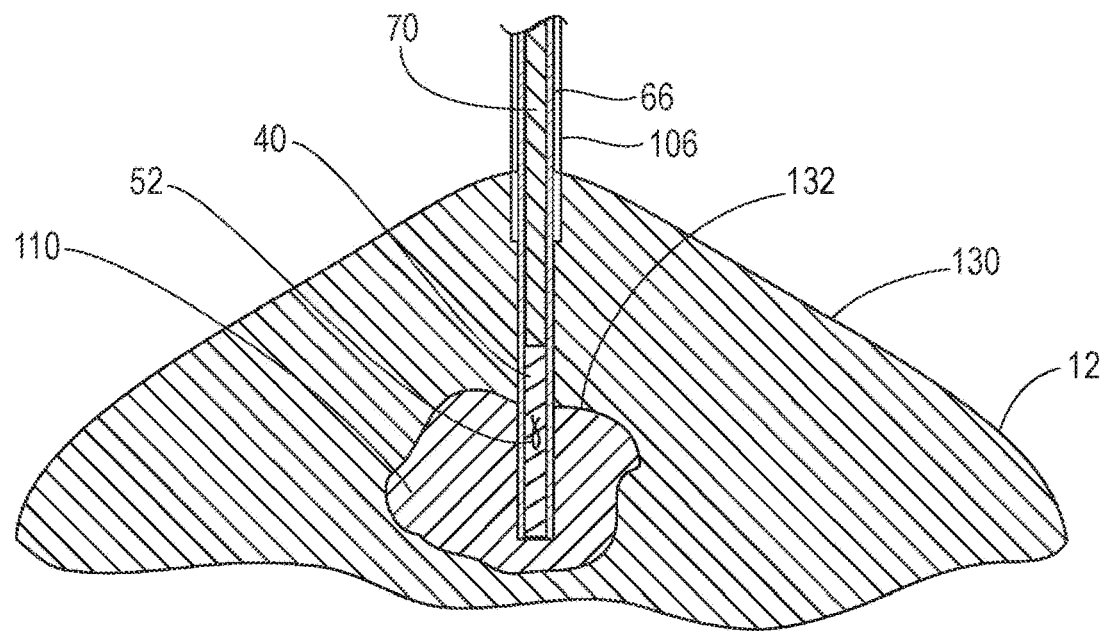
FIG. 35 shows an elevation view of a distal portion of a cannula of a loaded applicator disposed within a tumor of a patient's breast tissue with a first end of the composite gel marker disposed in the fundus of the void and a second end of the composite gel marker disposed adjacent an outer boundary of the tumor.
Figure 36:
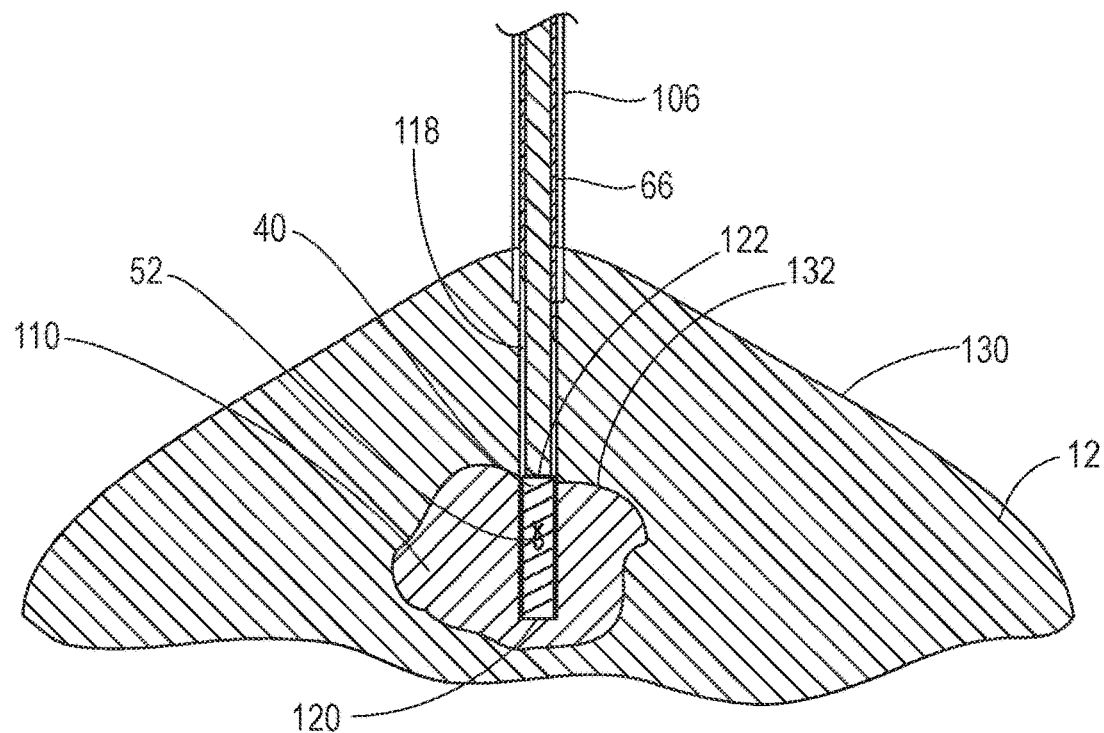
FIG. 36 shows the distal end of the cannula of the applicator being proximally retracted while a positioning rod of the applicator which remains substantially stationary with respect to tissue presses distally against the second end of the composite gel marker to maintain the axial position of the composite gel marker during the retraction of the cannula.
Figure 37:
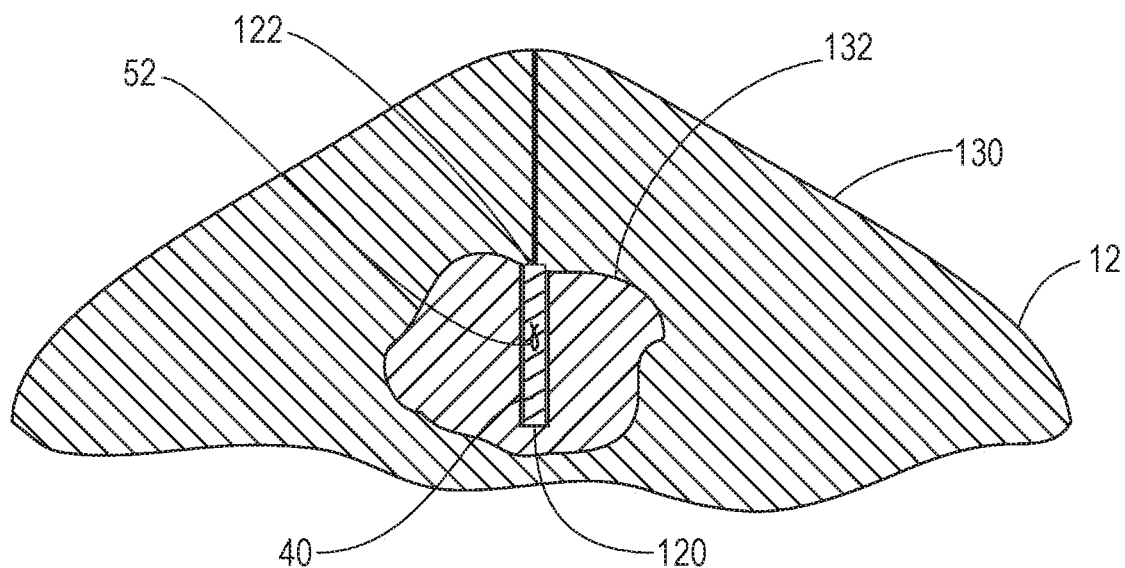
FIG. 37 shows the composite gel marker disposed within the tissue channel left by removal of the biopsy sample from the center of the tumor.

FIGS. 35-38 show a deployment method embodiment for deployment of one or more multi-mode composite gel markers 40 in breast tissue 130 in order to mark a target site lesion 110 within the breast tissue 130. A biopsy site and resulting channel 118 in the tissue of a tumor and surrounding tissue 130 may be created in the breast tissue 130 by the same biopsy methods and devices as those discussed above with regard to imaging and treatment of lung tissue 114. Thereafter, the cannula 66 of the applicator 56 loaded with one or more multi-mode composite gel markers 40 may be advanced through an inner lumen of an optional introducer 106 until the cannula 66 is disposed within a void 118 in a tumor 110 of a patient's breast tissue 130 with a first end 120 of the composite gel marker 40 disposed in the fundus or distal end of the void 118 substantially centered in the tumor 110 and a second end 122 of the composite gel marker 40 disposed adjacent an outer boundary 132 of the tumor 110 as shown in FIG. 35. After such positioning of the cannula 66, the distal end 82 of the cannula 66 of the applicator 56 may be proximally retracted while the positioning rod 70 of the applicator 56 presses distally against the second end 122 of the composite gel marker 40 to maintain the axial position of the composite gel marker 40 during the retraction of the cannula 66 as shown in FIG. 36. Thereafter, the cannula 66, positioning rod 70 and applicator 56 may be removed with the multi-mode composite gel marker 40 disposed within the tissue channel left by removal of the biopsy sample in the center of the tumor as shown in FIG. 37.

Figure 38:
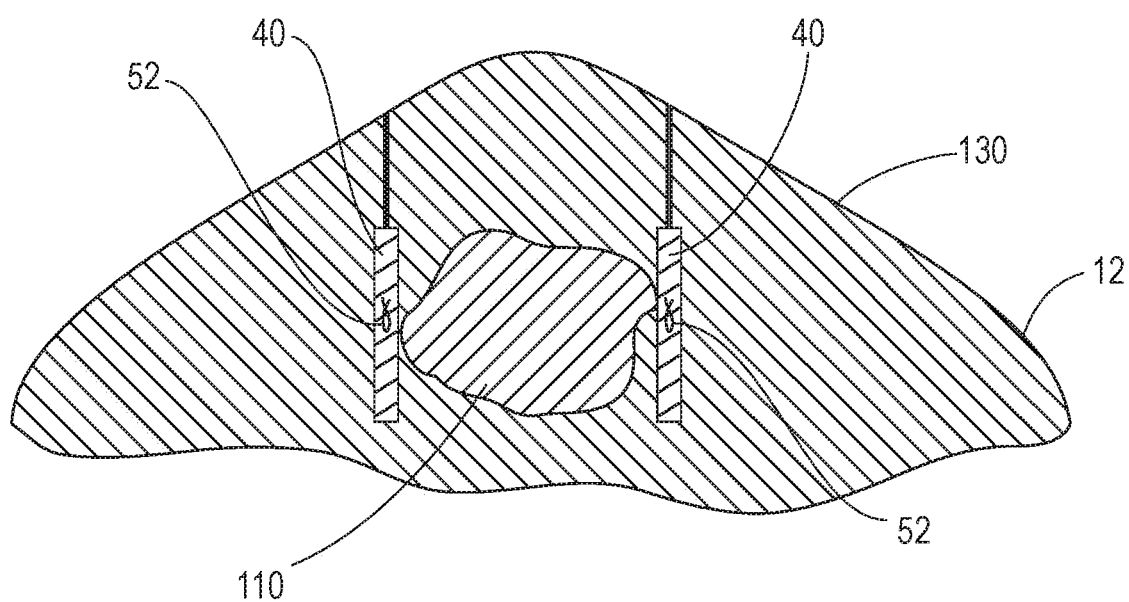
FIG. 38 shows two composite gel markers deployed by the method of FIGS. 35-37 disposed at opposite ends of a tumor disposed in breast tissue in order to mark a periphery of the tumor.

In some circumstances, rather than using such embodiments of the multi-mode composite gel marker 40 to mark the center of the tissue lesion or tumor 110 as shown in FIGS. 35-37, two or more composite gel markers 40 may be deployed by the method of FIGS. 35-37 in locations disposed at opposite ends of a tumor 110 in breast tissue 130 or any other tissue such as lung tissue 114 of a patient 12 in order to mark a periphery of a tissue lesion 110 such as a tumor as shown in FIG. 38. In addition, in some cases, it may be desirable to use an elongate composite gel marker 40 for such a method with a second end 122 of the composite gel marker 40 extending to or beyond a surface of the tissue in order to serve a dual purpose of marking the center of the tumor 110 as well as functioning as a localization "wire" or conduit in that it may be possible for a clinician to follow the path of the elongate composite gel marker 40 from the surface of the tissue to the center of the tumor 110. Such an elongate composite gel marker 40 may have dimension similar to those discussed above with regard to similar embodiments.

The composite gel marker embodiments 40 used for indications such as breast tumor imaging shown in FIGS. 35-38 may in some cases be shorter in axial length than composite gel markers 40 being used for imaging signal conduits as discussed above with regard to treatment and imaging of lung tissue 114. As such, pellet type composite gel marker embodiments 40 used primarily for marking the center of a tumor 110 may in some cases have a transverse dimension of about 1 mm to about 3 mm and an axial length of about 2 mm to about 10 mm. Some composite gel marker embodiments 40 for such indications may include a 2 mg/ml concentration of 2 μm ultrasound visible silica shells dispersed in a gelatin pellet. Composite gel marker embodiments 40 having a dimension of about 5 mm pellets may be deployed in a standard 14-gauge applicator 56. In some cases, such composite gel marker embodiments 40 may be wrapped with a radiopaque coil wire 134 such as is shown in the composite gel marker embodiment 40 FIG. 14. Such radiopaque coil wire 134 may include a thin wire of radiopaque imaging material 29 including gold, platinum, tantalum and the like. The radiopaque coil wire may also serve, in some cases, as a multi-mode marker. In particular, the radiopaque coil wire 134 may include drawn filled tube material that includes a radiopaque imaging material 29 in one layer and an MRI imaging material 29 in another layer. Embodiments of such radiopaque coil wires may have an outer transverse dimension of about 0.0005 inches to about 0.005 inches and may be configured to provide a radiopaque imaging signature as well as an MRI signature without creating a significant bloom in either of these modalities. Some composite gel marker embodiments 40 may include gelatin material 48 and 2 μm silica shells. Such a composite gel marker 40 may have an outer diameter of about 1.6 mm and a length of about 6 mm. Some composite gel marker embodiments 40 may include gelatin material 48 and 2 μm silica shells with an outer diameter of about 1.6 mm and a length of about 6 mm. Such an embodiment of a composite gel marker may also include a coiled wire such as the radiopaque coil wire 134 discussed above with the wire 134 having a diameter of about 0.12 mm and the wire forming a coiled configuration having a coil diameter of about 1.6 mm and a length of about 2 mm.

Embodiments illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation and use of such terms and expressions do not exclude any equivalents of the features shown and described or portions thereof, and various modifications are possible. The term "a" or "an" can refer to one of or a plurality of the elements it modifies (e.g., "a reagent" can mean one or more reagents) unless it is contextually clear either one of the elements or more than one of the elements is described. Thus, it should be understood that although embodiments have been specifically disclosed by representative embodiments and optional features, modification and variation of the concepts herein disclosed may be resorted to by those

The invention claimed is:

1. A method of manufacturing a composite gel marker, the method comprising:
   forming a plurality of silica shells, each of the plurality of silica shells including:
      a respective shell body having a layer which is formed from silica; and
      a hollow void disposed within an inner surface of the shell body;
   coating each of the silica shells of the plurality of silica shells with a hydrophobic coating that seals the hollow void within each silica shell; a radiopaque marker dispersed within the gel material
   after coating each of the plurality of silica shells with the hydrophobic coating, distributing the plurality of silica shells coated with the hydrophobic coating within a gel material.

2. The method of claim 1, further comprising:
   dispersing imaging material within the gel material.

3. The method of claim 1, further comprising:
   dispensing the gel material and distributed plurality of silica shells into a tubular mold;
   freezing the gel material and distributed plurality of silica shells within the tubular mold; and
   freeze drying the gel material and distributed plurality of silica shells within the tubular mold.

4. The method of claim 3, further comprising:
   removing the freeze dried gel material and distributed plurality of silica shells from the tubular mold; and
   compressing the freeze dried gel material and distributed plurality of silica shells thereby reducing a transverse dimension of the freeze dried gel material and distributed plurality of silica shells.

5. The method of claim 1 wherein distributing the plurality of silica shells within the gel material includes combining dry gel material with distilled water and the plurality of silica shells.

6. The method of claim 1 wherein forming each of the plurality of silica shells comprises:
   forming a respective first layer of silica over a respective spherical template;
   removing the respective spherical template, thereby forming a respective hollow void enclosed by an inner surface of the respective first layer of silica, before coating each of the silica shells of the plurality of silica shells with the hydrophobic coating.

7. The method of claim 1 wherein coating each of the silica shells of the plurality of silica shells with a hydrophobic coating includes coating an outer surface of each of the silica shells of the plurality of silica shells with the hydrophobic coating, further comprising:
   allowing the hydrophobic coating to dry on the outer surface of each of the silica shells before distributing the plurality of silica shells coated with the hydrophobic coating within the gel material.

8. The method of claim 7 wherein the plurality of silica shells are not exposed to a solvent after allowing the hydrophobic coating to dry on the outer surface of each of the silica shells.

9. The method of claim 7 wherein coating an outer surface of each of the silica shells of the plurality of silica shells with the hydrophobic coating includes coating the outer surface of each of the silica shells of the plurality of silica shells with a polymer.

10. The method of claim 7 wherein coating an outer surface of each of the silica shells of the plurality of silica shells with the hydrophobic coating includes coating the outer surface of each of the silica shells of the plurality of silica shells with a silane.

11. The method of claim 7 wherein coating an outer surface of each of the silica shells of the plurality of silica shells with the hydrophobic coating includes the outer surface of each of the silica shells of the plurality of silica shells with octyltriethoxysilane.

12. The method of claim 7 wherein coating an outer surface of each of the silica shells of the plurality of silica shells with the hydrophobic coating includes coating the outer surface of each of the silica shells of the plurality of silica shells with the hydrophobic coating that is about 0.1 percent to about 5.0 percent by weight of the total weight of the silica shells.

13. A method of manufacturing a composite gel marker, the method comprising:
   forming a respective first layer of silica over a each of a plurality of spherical templates;
   removing each of the plurality of spherical templates, thereby forming a plurality of hollow voids, each enclosed by an inner surface of the respective first layer of silica;
   encapsulating each of the respective first layer of silica and the enclosed hollow void within a hydrophobic coating, thereby forming a plurality of silica shells; and
   after forming the plurality of silica shells, distributing the plurality of silica shells within a gel material.

14. The method of claim 13, further comprising:
   dispensing the gel material and distributed plurality of silica shells into a tubular mold;
   freezing the gel material and distributed plurality of silica shells within the tubular mold;
   freeze drying the gel material and distributed plurality of silica shells within the tubular mold;
   removing the freeze dried gel material and distributed plurality of silica shells from the tubular mold; and
   compressing the freeze dried gel material and distributed plurality of silica shells thereby reducing a transverse dimension of the freeze dried gel material and distributed plurality of silica shells.

15. The method of claim 14, further comprising:
   removing air from the freeze dried gel material and distributed plurality of silica shells when compressing the freeze dried gel material and distributed plurality of silica shells.

16. The method of claim 14 wherein:
   compressing the freeze dried gel material and distributed plurality of silica shells includes rolling the freeze dried gel material and distributed plurality of silica shells under pressure, and
   rolling the freeze dried gel material and distributed plurality of silica shells under pressure is performed prior to removing the freeze dried gel material and distributed plurality of silica shells from the tubular mold.

17. The method of claim 13, further comprising:
dispersing imaging material within the gel material.

18. The method of claim 13, further comprising:
encapsulating a radiopaque marker within the gel material.

19. The method of claim 13 wherein:
each of the plurality of spherical templates includes a polystyrene bead with a diameter of between 50 nm and 2.2 microns; and
removing each of the plurality of spherical templates includes performing a calcination process at temperatures between about 530° C. and about 570° C. for about 5 hours.

* * * * *